US011162107B2

(12) United States Patent
Magneschi et al.

(10) Patent No.: US 11,162,107 B2
(45) Date of Patent: Nov. 2, 2021

(54) CHLOROPLAST TARGETING PEPTIDE SEQUENCE DERIVED FROM NANNOCHLOROPSIS PHOSPHORIBULOKINASE AND METHODS FOR USE

(71) Applicant: TOTAL RAFFINAGE CHIMIE, Courbevoie (FR)

(72) Inventors: Leonardo Magneschi, Edinburgh (GB); Eric Marechal, Grenoble (FR); Giovanni Finazzi, Fontaine (FR); Mariette Bedhomme, Vif (FR); Séverine Collin, Sassenage (FR); Frédéric Laeuffer, Paris (FR); Laurent Fourage, Suresnes (FR)

(73) Assignee: Total Raffinage Chimie, Courbevoie (FR)

( * ) Notice: Subject to any disclaimer, the term of this patent is extended or adjusted under 35 U.S.C. 154(b) by 0 days.

(21) Appl. No.: 16/465,599

(22) PCT Filed: Dec. 5, 2017

(86) PCT No.: PCT/EP2017/081451
§ 371 (c)(1),
(2) Date: May 31, 2019

(87) PCT Pub. No.: WO2018/104267
PCT Pub. Date: Jun. 14, 2018

(65) Prior Publication Data
US 2019/0352346 A1 Nov. 21, 2019

(30) Foreign Application Priority Data

Dec. 5, 2016 (EP) .................................... 16290225

(51) Int. Cl.
*C12N 15/82* (2006.01)
*A01G 33/00* (2006.01)
*C07K 14/405* (2006.01)
*C12N 5/04* (2006.01)
*C12N 9/12* (2006.01)

(52) U.S. Cl.
CPC ......... *C12N 15/8221* (2013.01); *A01G 33/00* (2013.01); *C07K 14/405* (2013.01); *C12N 5/04* (2013.01); *C12N 9/1205* (2013.01); *C12N 15/8214* (2013.01); *C12N 15/8257* (2013.01); *C07K 2319/08* (2013.01)

(58) Field of Classification Search
None
See application file for complete search history.

(56) References Cited

PUBLICATIONS

Jinkerson et al. Nannochloropsis gaditana CCMP526 NGA_Contig30754 mRNA sequence. (2012) GenBank Accession JU964798; pp. 1-2 (Year: 2012).*

UniProtKB—W7TMN7; Phosphoribulokinase "PRK" (2014) pp. 1-6 (Year: 2014).*
Jinkerson et al. Genomic insights from the oleaginous model alga Nannochloropsis gaditana. (2013) Bioengineered; vol. 4; pp. 37-42 (Year: 2013).*
Corteggiani et al. Phosphoribulokinase [Nannochloropsis gadtana], (2014) Gen Bank Accession EWM21954; pp. 1-2 (Year: 2014).*
Moog et al. In vivo localization studies in the stramenopile alga Nannochloropsis oceanica. (2015) Protist; vol. 166; pp. 161-171 (Year: 2015).*
Gavel et al. A conserved cleavage-site motif in chloroplast transit peptides. (1990) FEBS Letters; vol. 261; pp. 455-458 (Year: 1990).*
MOOG et al., "In vivo localization studies in the stramenopile alga Nannochloropsis oceanica.", PROTIST; Feb. 2015, vol. 166, No. 1, pp. 161-171.
Gruber et al., "Protein targeting into complex diatom plastids: functional characterisation of a specific targeting motif", Plant Molecular Biology, (2007), vol. 64, No. 5, pp. 519-530.
De Marchis et al., "Plastid Proteostasis and Heterologous Protein Accumulation in Transplastomic Plants1"; Plant Physiol., (Oct. 2012), vol. 160, pp. 571-581.
Muto et al., "Accumulation and processing of a recombinant protein designed as a cleavable fusion to the endogenous Rubisco LSU protein in Chlamydomonas chloroplast"; BMC Biotechnol., (2009), vol. 9, 26; pp. 1-11.
Lapidot et al., "Stable Chloroplast Transformation of the Unicellular Red Alga Porphyridium Species"; Plant Physiol., (May 2002), vol. 129, pp. 7-12.
Doetsch et al., "Chloroplast transformation in Euglena gracilis: splicing of a group III twintron transcribed from a transgenic psbK operon"; Curr Genet., (2001), vol. 39, pp. 49-60.
Xie et al., "Construction of Novel Chloroplast Expression Vector and Development of an Efficient Transformation System for the Diatom Phaeodactylum tricornutum"; Mar. Biotechnol, (2014), vol. 16, pp. 538-546.
Bhaya; Grossman, Targeting proteins to diatom plastids involves transport through an endoplasmic reticulum; Mol Gen Genet., (1991), vol. 229, pp. 400-404.
Lang et al., "Protein Transport into "Complex" Diatom Plastids Utilizes Two Different Targeting Signals"; J Biol Chem., (1998), vol. 273, No. 47; pp. 30973-30978.

(Continued)

*Primary Examiner* — Cathy Kingdon Worley
(74) *Attorney, Agent, or Firm* — Albert Shung

(57) ABSTRACT

The application generally relates to chloroplast targeting of nuclear-encoded proteins of interest in microalgae. Provided herein are expression cassettes comprising a nucleotide sequence encoding a chloroplast targeting peptide operably linked to a nucleotide sequence encoding a protein of interest, wherein said chloroplast targeting peptide comprises the bipartite targeting sequence of the phosphoribulokinase of *Nannochloropsis gaditana* (NgPRK BTS). The invention further provides vectors comprising the expression cassettes, and microalgae having stably incorporated or transiently expressed into their nuclear genomes an expression cassette described above. Methods are also provided for the production of a protein of interest in the chloroplast of a microalga, as well as methods for modulating chloroplast pathways.

14 Claims, 21 Drawing Sheets
Specification includes a Sequence Listing.

(56) References Cited

PUBLICATIONS

Tatusova; Madden, "Blast 2 Sequences, a new tool for comparing protein and nucleotide sequences"; FEMS Microbiol Lett, (1999), vol. 174, pp. 247-250.
Bowie et al., "Deciphering the Message in Protein Sequences: Tolerance to Amino Acid Substitutions"; Science, (Mar. 16, 1990), vol. 247, pp. 1306-1310.
Apt et al., "In vivo characterization of diatom multipartite plastid targeting signals"; J Cell Sci, (2002), vol. 115, issue 21; pp. 4061-4069.
Abida et al., "Membrane Glycerolipid Remodeling Triggered by Nitrogen and Phosphorus Starvation in Phaeodactylum tricornutum"; Plant Physiology, (Jan. 2015), vol. 167, No. 1, pp. 118-136.
Dong et al., "Responses of Nannochloropsis oceanica IMET1 to Long-Term Nitrogen Starvation and Recovery"; Plant Physiol., (Jun. 2013), vol. 162, No. 2, pp. 1110-1126.
Radakovits et al., "Draft genome sequence and genetic transformation of the oleaginous alga Nannochloropis gaditana"; (2012) Nat Commun 3:686; pp. 1-10.
International Search Report issued in Application No. PCT/EP2017/081451, dated Feb. 19, 2018, 4 pages.
"TSA: Nannochloropsis gaditana CCMP526 NGA_Contig30754 mRNA sequence.", EMBL, (May 17, 2012), Database accession No. JU964798, URL: EBI, XP002769907.
"RecName: Full=Phosphoribulokinase {ECO:0000256|RuleBase:RU004082}; EC=2.7.1.19 {ECO:0000256|RuleBase:RU004082};", UniProt, (Apr. 16, 2014), Database accession No. W7TMN7, URL: EBI, XP002769908.

* cited by examiner

FIG. 1A

SEQ ID NO:1

GTTGCGTAACACTTCTTCTGATGAGGTGCATTGGATGGTGTCGTACGTGTTTTCGCCTCCTCGT
CCACACCATCCGACTGTTTGTACCCATGATGACGCGATCACACCGTCTTCACGGGTTGGGACAC
TGTCGTCTTGCTGTTTGTCAACGTGCCACGCTACCTCGCCTTCGACAAAGATCTCCATGCCATC
CGCGGCCGGGAATACCTGGATTTTGGCATAGCTCCCACATCATGGGGAAATTCGGCATGCCACA
CCGCTCATTTAACTCCTGAGCGCTGCAACATGTGCAAGCCAAGCGCCAAGACGCCCGAGCCACT
TGTTCAGTTCTCAAGAGGGGCCGGGAGGATCGTCGCGGGCTTCGATGAAAGCGTCTcCGCTTCA
GTTTAAGCCCCAGCGTCATTCATAGTCACGTTGTTTTCTCACAAAATCTCATTTTTCCTTGCA
GAAGTATGGTCAAGACTGCCGCCGTAAGCCTCCTGGCCCTAGCCGGGCTCGCATCTGCCTTCGT
GCCCCCCACCACGAATTTTCGCAGCGCTAACAGATGGACGATTAAGGCCAAAGACACGTCCTTC
ACCCGCAACCTCATGATGAAGCTGGGCGCGGACGACAAGGTCATTTGATCGGCGTGGCCGCGG
ATTCCGGCTGTGGAAAGTCGACGTTCATGCGGCGGCTGACCAACATCTTTGGTGGGAGCAACGT
GGGCCCCCTgGGGGGCGGTTTCGACAACGGGGGATGGGAGACGAACACCCTGGTCTCGGACACG
ACCACCGTCATCTGCTTGGACGACTACCATGCCAACGACCGCTCTGGGCGGAAAGTGACGGGCC
GCACCGCCTTGGAAGCTGCCGAGCAGAATTTTGACCTCATGTACGAGCAGCTCAAGGCCCTGAA
GGAGGGCAAAACTGTGGCCAAGCCCATCTACAACCACGTGAACGGGACCTTGGACCGGCCCGAG
GAGGTGGTGCCCACCCCCATTGTGATCGTGGAGGGCTTGCACCCCTGGTACGACGCCCGCGTCA
AGGACCTGCTCGACTACACTATCTACCTGGACATATCGGACGAGATCAAGCGCGCATGGAAGAT
CCAGCGGGACATGGCCGAGCGCGGATGGACCTTGGAGCAGGTGGAGGCAGAGATTGAAAAGCGT
AAGCCGGACTTCAATAAATTCGTGGGGCCCCAGAAGGAGGTAGCCGACTCGGTGATCCAAGTCT
TGCCCACAGAGCTGACCAACGACCCCGAGGGGAAGATCCTCCGCGTCCGGCTCATCCAGAAGGA
GACGGGGGACTACGAACCCGTCTACCTGTTCGACCAGGGCTCTACGGTCTCCTGGATTCCCTGC
GGCACGAAGCTGACATGCTCCTACCCCGGCATCAAGCTGGGCTCGGGACCGGACCGCTGGTTCA
ACAACGCGGTGAACGTGGTGGAGATGGACGGCCAGTTTGACAAGCTGGAAGAGCTTGCCTACGT
GGAGAAGCACCTGGGGAACACGGCCAGCAAGTACGACgGGGAGATCACGGcCCAGATGCTCAAG
aACgAgGGCCCCCGGGACCCTGAACGGCTCAGGCCTCTTCCAGACCATCGTCTCGCTCAAGATC
CGCGAGGTCTACGAGAAGCTGAGCGGGAAGAAGGTAGACGCCTCCGTCAAGGCCCCCGTGGCCG
CGTAAGCCGGCGGCAAAGGAGCGAGGGCTGGTTGGCTGCTGAAAACAGGGTAGGCTTTGAGGTG
TGGAGATCGTAACGGCTCCCACCGGACCTCAGCAGCATCCCTTGAACAAACGGCGAGCCTCACA
CGCCGACTGCTGCATGTTTTGTGTGTTCTGTGCTTTTCGTGTCCGGAGCCATCGCGTCGTCTGC
GCCGGGTGCCGGGCCCAGAGAGCgGGGGGAGGGCCAGGGAGGCATTCTGTTGTTTTGGGTGGTG
TTTGGGGGATAGGAGACTGACCTGTCGGCCCCTTTTTGACGTATCGCGAATTTCGATGAAATAA
TCGGCTCCATTCTCCATTAAATTGAAGCATGCATGGATGATGATCGAGGTGGGAGGGGCGCCTA
TAACACCGCCACCTGTGTCCCTGGGCGAGCTCTTCGGGTTCCTTTACTTTCGACTCCGAAAAC
GCTTTTCTGAAACAAAGTCGCCAAGGTTACTCGCTGTTGCCCATACCCCTTCCATTCGCGAGTC
TAGAACTCCTTGCAGATCCCTGGATAAGAGATTCAAAAACGTTGCGGCCGAGGAGTCGATGGAA
TGCCTCCCTCCTTGAACCCGCCCGGCCTGCGCGTGCTCATGGCTCGTGACAGACACCCATGTCG
ACCTCGCCTGCGGGAGAGAAACAGAGCGTCCGAAAACAGCGCAAAGGGAGTCCGAGAACTGCGC
AAAGAAAGTCCGAGAGCAGCGCGCAGCAAAAGCGAGGGTCCTTGTGGCCTGATTTCATCGTGGA
AGATGTTACGAATCACGACTTATGCGCACCACTTCACTTCATCGAAGCGCGATCCTGTTTATAC
TTTCTACTGCACAAAATTGTGTGTCGATCCCCTCCTTCTCCCCCTCTCCTCCTCTCCCTCGCCT
CACTCATCTAAATGGCGTGCCAGCACATGATAGGTGGCGTCATAGCAGGGTAAAATTACACTGG
CCACGGGCACGGCC

FIG. 1B

SEQ ID NO:2

MVKTAAVSLLALAGLASAFVPPTTNFRSANRWTIKAKDTSFTRNLMMKLGADDKVILIGVAADS
GCGKSTFMRRLTNIFGGSNVGPLGGGFDNGGWETNTLVSDTTTVICLDDYHANDRSGRKVTGRT
ALEAAEQNFDLMYEQLKALKEGKTVAKPIYNHVNGTLDRPEEVVPTPIVIVEGLHPWYDARVKD
LLDYTIYLDISDEIKRAWKIQRDMAERGWTLEQVEAEIEKRKPDFNKFVGPQKEVADSVIQVLP
TELTNDPEGKILRVRLIQKETGDYEPVYLFDQGSTVSWIPCGTKLTCSYPGIKLGSGPDRWFNN
AVNVVEMDGQFDKLEELAYVEKHLGNTASKYDGEITAQMLKNEGPRDPERLRPLPDHRLAQDPR
GLREAEREEGRRLRQGPRGRVSRRQRSEGWLAAENRVGFEVWRS

FIG. 2

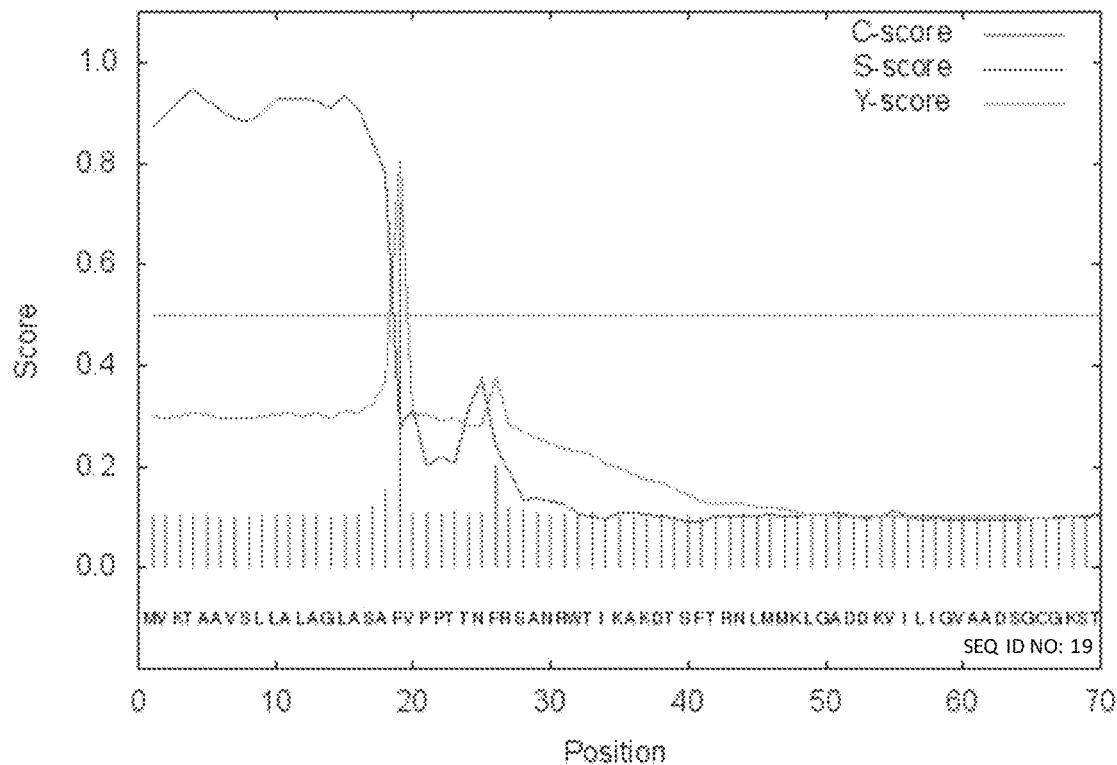

FIG. 3A

SEQ ID NO: 3: AT1G32060.1 (*Arabidopsis thaliana*)

MAVSTIYSTQALNSTHFLTSSSSSKQVFLYRRQPQTNRRFNTLITCAQETIVIGLAADSGCGKS
TFMRRLTSVFGGAAKPPKGGNPDSNTLISDTTTVICLDDYHSLDRYGRKEQKVTALDPRANDFD
LMYEQVKALKNGIAVEKPIYNHVTGLLDPPELIQPPKILVIEGLHPMFDERVRDLLDFSIYLDI
SNEVKFAWKIQRDMAERGHSLESIKASIEARKPDFDAFIDPQKQYADAVIEVLPTTLIPDDNEG
KVLRVRLIMKEGVKYFSPVYLFDEGSTISWIPCGRKLTCSYPGIKFNYEPDSYFDHEVSVLEMD
GQFDRLDELIYVESHLSNLSTKFYGEVTQQMLKHADFPGSNNGTGLFQTIVGLKIRDLYEQLIA
NKATARAEAKA

FIG. 3B

SEQ ID NO:4: Spinach_P09559 (*Spinacia oleracea*)

MAVCTVYTIPTTTHLGSSFNQNNKQVFFNYKRSSSSNNTLFTTRPSYVITCSQQQTIVIGLAAD
SGCGKSTFMRRLTSVFGGAAEPPKGGNPDSNTLISDTTTVICLDDFHSLDRNGRKVEKVTALDP
KANDFDLMYEQVKALKEGKAVDKPIYNHVSGLLDPPELIQPPKILVIEGLHPMYDARVRELLDF
SIYLDISNEVKFAWKIQRDMKERGHSLESIKASIESRKPDFDAYIDPQKQHADVVIEVLPTELI
PDDDEGKVLRVRMIQKEGVKFFNPVYLFDEGSTISWIPCGRKLTCSYPGIKFSYGPDTFYGNEV
TVVEMDGMFDRLDELIYVESHLSNLSTKFYGEVTQQMLKHQNFPGSNNGTGFFQTIIGLKIRDL
FEQLVASRSTATATAAKA

FIG. 3C

SEQ ID NO:5: Pt_CCAP1055/1 (*Phaeodactylum tricornutum*)

MKFAVFASLTATAAAFAPTAFVPSNLRGVAPSASSLNMALKEGQTPIIIGVAADSGCGKSTFMR
RLTNIFGGDVVGPLGGGFDKGSWETNTLVSDLTTVICLDDYHLNDRAGRKVTMRTALDPEENNF
DLMYEQVKALKDGKTVEKPIYNHVNGTLDTPETIEPTPIIIFEGLHPMHDKRVLDLLDFSLYLD
ISDDVKLNWKVQRDMEERGHSMESILASIEARKPDFDAYIDPQKQLADLIIEVLPTRLDQDDKK
TLRVRCIQKEGVENFDPCFLFDEGSSIEWTPAPTKLSSPAPGIKLAYYPEEFFGKDAQVLEMDG
NFDNIQELVYVESALSNTKTKFYGEMTQAMLALATAPGSNNGTGLMQTLAAFAIRDIYEKKTAA
AKAKAGVSAAAA

FIG. 3D

SEQ ID NO:6: Cr_XP_001694038 (*Chlamydomonas reinhardtii*)

MAFTMRAPAPRATAQSRVTANRARRSLVVRADKDKTVVIGLAADSGCGKSTFMRRMTSIFGGVP
KPPAGGNPDSNTLISDMTTVICLDDYHCLDRNGRKVKGVTALAPEAQNFDLMYNQVKALKEGKS
VDKPIYNHVSGLIDAPEKIESPPILVIEGLHPFYDKRVAELLDFKIYLDISDDIKFAWKIQRDM
AERGHSLESIKSSIAARKPDFDAYIDPQKKDADMIIQVLPTQLVPDDKGQYLRVRLIMKEGSKM
FDPVYLFDEGSTISWIPCGRKLTCSFPGIKMFYGPDTWYGQEVSVLEMDGQFDKLEELIYVESH
LSNTSAKFYGEITQQMLKNSGFPGSNNGTGLFQTIVGLKVREVYERIVKKDVVPV

FIG. 3E

SEQ ID NO: 7: Os02g0698000 (*Oryza sativa*)

MAISSLHATTSLHSPCTTNTSFRQNQVIFFTTRSNRRGSTRYGGARTFQVSCSVDKPVVIGLAA
DSGCGKSTFMRRLTSVFGGAAEPPKGGNPDSNTLISDTTTVICLDDYHSLDRTGRKEKGVTALD
PRANDFDLMYEQVKAIKEGKAIEKPIYNHVTGLLDPPELIQPPKIFVIEGLHPMFDERVRDLLD
FSIYLDISDEVKFAWKIQRDMAERGHSLESIKASIEARKPDFDAFIDPQKQYADAVIEVLPTQL
IPDDNEGKVLRVKLIMKEGVKNFNPVYLFDEGSSITWVPCGRKLTCSYPGIKFAYGPDTYFGHE
VSVLEMDGQFDRLDELIYVESHLSNLSTKFYGEVTQQMLKHADFPGSNNGTGLFQTIVGLKIRD
LYEQIIAERAGAPTEAAKV

FIG. 4

```
Query  1    MVKTAAVSLLALAGLASAFVPPTTNFRSANRWTIKAKDTSFTRNLMMKLGADDKVILIGV 60
Helix  1    HHHHHHHHHHHHHHHHH        HHHHHHHHHHHHHHHHHHHHHHH           60
Sheet  1    EEEEEEEEEEEEEEEEEEEEEEE       EE    EEEEEEEEEE      EEEEE   60
Turns  1                          T   T    T T      T  T       T       60

*         *         *         *         *
Query  61   AADSGCGKSTFMRRLTNIFGGSNVGPLGGGFDNGGWETNTLVSDTTTVICLDDYHANDRS 120
Helix  61   HH                                         HHHHHHHHHH       120
Sheet  61         EEEEEEEEEEEE              EEEEEEEEEEEEEEEEEEEE        120
Turns  61       T   TT            TT      T  TT   T       T          T  120

*         *         *         *         *
Query  121  GRKVTGRTALEAAEQNFDLMYEQLKALKEGKTVAKPIYNHVNGTLDRPEEVVPTPIVIVE 180
Helix  121            HHHHHHHHHHHHHHHHHHHHHHH            HHHHHHHHHHHH   180
Sheet  121     EEEE       EEEEEEEEEEEE      EEEEEEEEEEEEE    EEEEEEEEEE 180
Turns  121  T   T           T             TT    T       T   T T     T   180

*         *         *         *         *
Query  181  GLHPWYDARVKDLLDYTIYLDISDEIKRAWKIQRDMAERGWTLEQVEAEIEKRKPDFNKF 240
Helix  181  HH    HHHHHHHH     HHHHHHHHHHHHHHHHHHHHHHHHHHHHHHHHHHHHHHH  240
Sheet  181  EEEEE    EEEEEEEEEEEEE       EEEEEE    EEEEE          EEEE  240
Turns  181          T                T       T    T        T   T  T    240

*         *         *         *         *
Query  241  VGPQKEVADSVIQVLPTELTNDPEGKILRVRLIQKETGDYEPVYLFDQGSTVSWIPCGTK 300
Helix  241  HHHHHHHHHHHHHHHHH        HHHHHHHHHHH       HHHHHHH           300
Sheet  241  EEE    EEEEEEEEEEEE           EEEEEEEEE    EEEEEEEEEEEEEEEEEE 300
Turns  241     T T    T         T    TT  T          T T           TT     T 300

*         *         *         *         *
Query  301  LTCSYPGIKLGSGPDRWFNNAVNVVEMDGQFDKLEELAYVEKHLGNTASKYDGEITAQML 360
Helix  301                  HHHHHHHHHHHHHHHHHHHHHHHHHHHH           HHHHHH 360
Sheet  301  EEEEEEEE           EEEEEEEEEEEEEEEEEEEEEEE         EEEEEEEEE 360
Turns  301              T  T    T       T            T T    T T T       360

*         *         *         *         *
Query  361  KNEGPRDPERLRPLPDHRLAQDPRGLREAEREEGRRLRQGPRGRVSRRQRSEGWLAAENR 420
Helix  361  HH           HHHHHHH    HHHHHHH                HHHHHHHHHHHH 420
Sheet  361                                                              420
Turns  361      T       T           T T    T  T T   T    T    T       T 420

Query  421  VGFEVWRS 428
Helix  421  HHHHH    428
Sheet  421  EEEEE    428
Turns  421           428

Total Residues: H: 260   E: 238   T: 67
Percent: H: 60.7  E: 55.6  T: 15.7
```

FIG. 5A

SEQ ID NO:13: pCT2*Ng*:

GTGGCACTTTTCGGGGAAATGTGCGCGGAACCCCTATTTGTTTATTTTTCTAAATACATTCAAA
TATGTATCCGCTCATGAGACAATAACCCTGATAAATGCTTCAATAATATTGAAAAAGGAAGAGT
ATGAGTATTCAACATTTCCGTGTCGCCCTTATTCCCTTTTTTGCGGCATTTTGCCTTCCTGTTT
TTGCTCACCCAGAAACGCTGGTGAAAGTAAAAGATGCTGAAGATCAGTTGGGTGCACGAGTGGG
TTACATCGAACTGGATCTCAACAGCGGTAAGATCCTTGAGAGTTTTCGCCCCGAAGAACGTTTT
CCAATGATGAGCACTTTTAAAGTTCTGCTATGTGGCGCGGTATTATCCCGTATTGACGCCGGGC
AAGAGCAACTCGGTCGCCGCATACACTATTCTCAGAATGACTTGGTTGAGTACTCACCAGTCAC
AGAAAAGCATCTTACGGATGGCATGACAGTAAGAGAATTATGCAGTGCTGCCATAACCATGAGT
GATAACACTGCGGCCAACTTACTTCTGACAACGATCGGAGGACCGAAGGAGCTAACCGCTTTTT
TGCACAACATGGGGATCATGTAACTCGCCTTGATCGTTGGGAACCGGAGCTGAATGAAGCCAT
ACCAAACGACGAGCGTGACACCACGATGCCTGTAGCAATGGCAACAACGTTGCGCAAACTATTA
ACTGGCGAACTACTTACTCTAGCTTCCCGGCAACAATTAATAGACTGGATGGAGGCGGATAAAG
TTGCAGGACCACTTCTGCGCTCGGCCCTTCCGGCTGGCTGGTTTATTGCTGATAAATCTGGAGC
CGGTGAGCGTGGGTCTCGCGGTATCATTGCAGCACTGGGGCAGATGGTAAGCCCTCCCGTATC
GTAGTTATCTACACGACGGGGAGTCAGGCAACTATGGATGAACGAAATAGACAGATCGCTGAGA
TAGGTGCCTCACTGATTAAGCATTGGTAACTGTCAGACCAAGTTTACTCATATATACTTTAGAT
TGATTTAAAACTTCATTTTTAATTTAAAAGGATCTAGGTGAAGATCCTTTTTGATAATCTCATG
ACCAAAATCCCTTAACGTGAGTTTTCGTTCCACTGAGCGTCAGACCCCGTAGAAAAGATCAAAG
GATCTTCTTGAGATCCTTTTTTTCTGCGCGTAATCTGCTGCTTGCAAACAAAAAAACCACCGCT
ACCAGCGGTGGTTTGTTTGCCGGATCAAGAGCTACCAACTCTTTTTCCGAAGGTAACTGGCTTC
AGCAGAGCGCAGATACCAAATACTGTCCTTCTAGTGTAGCCGTAGTTAGGCCACCACTTCAAGA
ACTCTGTAGCACCGCCTACATACCTCGCTCTGCTAATCCTGTTACCAGTGGCTGCTGCCAGTGG
CGATAAGTCGTGTCTTACCGGGTTGGACTCAAGACGATAGTTACCGGATAAGGCGCAGCGGTCG
GGCTGAACGGGGGGTTCGTGCACACAGCCCAGCTTGGAGCGAACGACCTACACCGAACTGAGAT
ACCTACAGCGTGAGCTATGAGAAAGCGCCACGCTTCCCGAAGGGAGAAAGGCGGACAGGTATCC
GGTAAGCGGCAGGGTCGGAACAGGAGAGCGCACGAGGGAGCTTCCAGGGGGAAACGCCTGGTAT
CTTTATAGTCCTGTCGGGTTTCGCCACCTCTGACTTGAGCGTCGATTTTTGTGATGCTCGTCAG
GGGGGCGGAGCCTATGGAAAAACGCCAGCAACGCGGCCTTTTTACGGTTCCTGGCCTTTTGCTG
GCCTTTTGCTCACATGTTCTTTCCTGCGTTATCCCCTGATTCTGTGGATAACCGTATTACCGCC
TTTGAGTGAGCTGATACCGCTCGCCGCAGCCGAACGACCGAGCGCAGCGAGTCAGTGAGCGAGG
AAGCGGAAGAGCGCCCAATACGCAAACCGCCTCTCCCCGCGCGTTGGCCGATTCATTAATGCAG
CTGGCACGACAGGTTTCCCGACTGGAAAGCGGGCAGTGAGCGCAACGCAATTAATGTGAGTTAG
CTCACTCATTAGGCACCCCAGGCTTTACACTTTATGCTTCCGGCTCGTATGTTGTGTGGAATTG
TGAGCGGATAACAATTTCACACAGGAAACAGCTATGACCATGATTACGCCAAGCGCGCAATTAA
CCCTCACTAAAGGGAACAAAAGCTGGAGCTCAGCTGCTGCCCCGACCGTATCTCCAAGTCAGAC
ATGAAATCTTCAGTTGCGTTAAAAACTCTACGATGCTACCAGCGTTAAATAACCTTGCCCACGC
CTTTAAACGTACCCGATCATTAACATATCGACTGGCTGCCTTGGCTTTGCACCAGCCATCATCA
GACTTAACGATGGGTATGTTGCTTGCCTTTCCTGCTTGAAGGGGGTCCGACTCTCTGCTTTCTC
GATCGCGGGTGTGACCTCTGAATTGGAATGTAAAAATGTAAGAAGCGACGTGTCCGGTAAAGAA
ATGCCCAAGCTCCATCAAATCTGCGTTGTCGGCGACCAAACCATGCTGGCTCGTCGACCTGCCC
CGGATGCAGGAGCATGGCACTCGGCGGCATGGCACTTGAGCCTCGCGGGAGGAATGTGTGTGGT

FIG. 5A (cont.)

```
TGGGCGCAGGCTGTGGACGGCCCCCCTCCAGCGAAGCGGTCGCCTCCCTTTCCGACGCTTTGTG
CACGTTGTCTGGTGTCCTCTGTCTCACGCACCTCTTCACCGACGTGGTGTCCCTCTTGTTGCTG
GTGAGGGACTTGGAATGTGGTCCTGGTTCTATCCTGGGCGCGTGTGTTCCTTTTTTTCTCTACC
GTTATTCTCTCCATTTCTGATGTCTCACCACCATCTCCCTCACCCTCCAACCGCGTCGTTGTGC
CAAAATCATACAGCAGGATCGATGGCCAAGTTGACCAGTGCCGTTCCGGTGCTCACCGCGCGCG
ACGTCGCCGGAGCGGTCGAGTTCTGGACCGACCGGCTCGGGTTCTCCCGGGACTTCGTGGAGGA
CGACTTCGCCGGTGTGGTCCGGGACGACGTGACCCTGTTCATCAGCGCGGTCCAGGACCAGGTG
GTGCCGGACAACACCCTGGCCTGGGTGTGGGTGCGCGGCCTGGACGAGCTGTACGCCGAGTGGT
CGGAGGTCGTGTCCACGAACTTCCGGGACGCCTCCGGGCCGGCCATGACCGAGATCGGCGAGCA
GCCGTGGGGCGGGAGTTCGCCCTGCGCGACCCGGCCGGCAACTGCGTGCACTTCGTGGCCGAG
GAGCAGGACTAAATCGATCTTCCTTAAAAATTTAATTTTCATTAGTTGCAGTCACTCCGCTTTG
GTTTCACAGTCAGGAATAACACTAGCTCGTCTTCACCATGGATGCCAATCTCGCCTATTCATGG
TGTATAAAAGTTCAACATCCAAAGCTAGAACTTTTGGAAAGAGAAAGAATATCCGAATAGGGCA
CGGCGTGCCGTATTGTTGGAGTGGACTAGCAGAAAGTGAGGAAGGCACAGGATGAGTTTTCTCG
AGAGCTGCTGCCCCGACCGTATCTCCAAGTCAGACATGAAATCTTCAGTTGCGTTAAAAACTCT
ACGATGCTACCAGCGTTAAATAACCTTGCCCACGCCTTTAAACGTACCCGATCATTAACATATC
GACTGGCTGCCTTGGCTTTGCACCAGCCATCATCAGACTTAACGATGGGTATGTTGCTTGCCTT
TCCTGCTTGAAGGGGGTCCGACTCTCTGCTTTCTCGATCGCGGGTGTGACCTCTGAATTGGAAT
GTAAAAATGTAAGAAGCGACGTGTCCGGTAAAGAAATGCCCAAGCTCCATCAAATCTGCGTTGT
CGGCGACCAAACCATGCTGGCTCGTCGACCTGCCCCGGATGCAGGAGCATGGCACTCGGCGGCA
TGGCACTTGAGCCTCGCGGGAGGAATGTGTGTGGTTGGGCGCAGGCTGTGGACGGCCCCCCTCC
AGCGAAGCGGTCGCCTCCCTTTCCGACGCTTTGTGCACGTTGTCTGGTGTCCTCTGTCTCACGC
ACCTCTTCACCGACGTGGTGTCCCTCTTGTTGCTGGTGAGGGACTTGGAATGTGGTCCTGGTTC
TATCCTGGGCGCGTGTGTTCCTTTTTTTCTCTACCGTTATTCTCTCCATTTCTGATGTCTCACC
ACCATCTCCCTCACCCTCCAACCGCGTCGTTGTGCCAAAATCATACAGCAGGAGGCCTGTCGAC
GGCGCGCCGGATCCAGATCTGAATTCGATATCACGCGTCCATGGCATATGGCTAGCGCGGCCGC
CTCGAGTCTAGACTTCCTTAAAAATTTAATTTTCATTAGTTGCAGTCACTCCGCTTTGGTTTCA
CAGTCAGGAATAACACTAGCTCGTCTTCACCATGGATGCCAATCTCGCCTATTCATGGTGTATA
AAAGTTCAACATCCAAAGCTAGAACTTTTGGAAAGAGAAAGAATATCCGAATAGGGCACGGCGT
GCCGTATTGTTGGAGTGGACTAGCAGAAAGTGAGGAAGGCACAGGATGAGTTTCTCGAGGGTA
CCCAATTCGCCCTATAGTGAGTCGTATTACGCGCGCTCACTGGCCGTCGTTTTACAACGTCGTG
ACTGGGAAAACCCTGGCGTTACCCAACTTAATCGCCTTGCAGCACATCCCCTTTCGCCAGCTG
GCGTAATAGCGAAGAGGCCCGCACCGATCGCCCTTCCCAACAGTTGCGCAGCCTGAATGGCGAA
TGGGACGCGCCCTGTAGCGGCGCATTAAGCGCGGCGGGTGTGGTGGTTACGCGCAGCGTGACCG
CTACACTTGCCAGCGCCCTAGCGCCCGCTCCTTTCGCTTTCTTCCCTTCCTTTCTCGCCACGTT
CGCCGGCTTTCCCCGTCAAGCTCTAAATCGGGGGCTCCCTTTAGGGTTCCGATTTAGTGCTTTA
CGGCACCTCGACCCCAAAAAACTTGATTAGGGTGATGGTTCACGTAGTGGGCCATCGCCCTGAT
AGACGGTTTTTCGCCCTTTGACGTTGGAGTCCACGTTCTTTAATAGTGGACTCTTGTTCCAAAC
TGGAACAACACTCAACCCTATCTCGGTCTATTCTTTTGATTTATAAGGGATTTTGCCGATTTCG
GCCTATTGGTTAAAAAATGAGCTGATTTAACAAAAATTTAACGCGAATTTTAACAAAATATTAA
CGCTTACAATTTAG
```

FIG. 5B

SEQ ID NO: 14: pCT55 cassette

GAATTCATGAGATCCTTTTGCATCGCAGCCCTTTTGGCTGTGGCATCTGCCTTCACCACACAGC
CAACTTCCTTCACTGTGAAGACTGCGAATGTGGGCGAACGGGCGAGTGGGGTTTTCCCTGAGCA
GAGCTCTGCTCATCGCACGCGTAAAGCAACGATTGTCATGGTCTCCAAGGGCGAGGAGCTCTTC
ACCGGCGTCGTCCCCATCCTCGTCGAGCTCGACGGCGACGTCAACGGCCACAAGTTCTCCGTCT
CCGGCGAGGGCGAGGGCGACGCTACCTACGGCAAGCTCACCCTCAAGTTCATCTGCACCACCGG
CAAGCTCCCCGTCCCCTGGCCCACCCTCGTCACCACCTTCGGCTACGGCCTCCAGTGCTTCGCT
CGCTACCCCGACCACATGAAGCAGCACGACTTCTTCAAGTCCGCTATGCCCGAGGGCTACGTCC
AGGAGCGCACCATCTTCTTCAAGGACGACGGCAACTACAAGACCCGCGCTGAGGTCAAGTTCGA
GGGCGACACCCTCGTCAACCGCATCGAGCTCAAGGGCATCGACTTCAAGGAGGACGGCAACATC
CTCGGCCACAAGCTCGAGTACAACTACAACTCCCACAACGTCTACATCATGGCTGACAAGCAGA
AGAACGGCATCAAGGTCAACTTCAAGATCCGCCACAACATCGAGGACGGCTCCGTCCAGCTCGC
TGACCACTACCAGCAGAACACCCCCATCGGCGACGGCCCCGTCCTCCTCCCCGACAACCACTAC
CTCTCCTACCAGTCCGCTCTCTCCAAGGACCCCAACGAGAAGCGCGACCACATGGTCCTCCTCG
AGTTCGTCACCGCTGCTGGCATCACCCTCGGCATGGACGAGCTCTACAAGTAACATATG

FIG. 5C

SEQ ID NO: 15: pCT56 cassette

GAATTCATGGTCAAGACTGCCGCCGTAAGCCTCCTGGCCCTAGCCGGGCTCGCATCTGCCTTCG
TGCCCCCCACCACGAATTTTCGCAGCGCTAACAGATGGACGATTAAGGCCAAAGACACGTCCTT
CACCCGCAACCTCATGATGAAGCTGGGCGCGGACGTCTCCAAGGGCGAGGAGCTCTTCACCGGC
GTCGTCCCCATCCTCGTCGAGCTCGACGGCGACGTCAACGGCCACAAGTTCTCCGTCTCCGGCG
AGGGCGAGGGCGACGCTACCTACGGCAAGCTCACCCTCAAGTTCATCTGCACCACCGGCAAGCT
CCCCGTCCCCTGGCCCACCCTCGTCACCACCTTCGGCTACGGCCTCCAGTGCTTCGCTCGCTAC
CCCGACCACATGAAGCAGCACGACTTCTTCAAGTCCGCTATGCCCGAGGGCTACGTCCAGGAGC
GCACCATCTTCTTCAAGGACGACGGCAACTACAAGACCCGCGCTGAGGTCAAGTTCGAGGGCGA
CACCCTCGTCAACCGCATCGAGCTCAAGGGCATCGACTTCAAGGAGGACGGCAACATCCTCGGC
CACAAGCTCGAGTACAACTACAACTCCCACAACGTCTACATCATGGCTGACAAGCAGAAGAACG
GCATCAAGGTCAACTTCAAGATCCGCCACAACATCGAGGACGGCTCCGTCCAGCTCGCTGACCA
CTACCAGCAGAACACCCCCATCGGCGACGGCCCCGTCCTCCTCCCCGACAACCACTACCTCTCC
TACCAGTCCGCTCTCTCCAAGGACCCCAACGAGAAGCGCGACCACATGGTCCTCCTCGAGTTCG
TCACCGCTGCTGGCATCACCCTCGGCATGGACGAGCTCTACAAGTAACATATG

FIG. 5D

SEQ ID NO: 16: pCT59 cassette

GAATTCATGGTCTCCAAGGGCGAGGAGCTCTTCACCGGCGTCGTCCCCATCCTCGTCGAGCTCG
ACGGCGACGTCAACGGCCACAAGTTCTCCGTCTCCGGCGAGGGCGAGGGCGACGCTACCTACGG
CAAGCTCACCCTCAAGTTCATCTGCACCACCGGCAAGCTCCCCGTCCCCTGGCCCACCCTCGTC
ACCACCTTCGGCTACGGCCTCCAGTGCTTCGCTCGCTACCCCGACCACATGAAGCAGCACGACT
TCTTCAAGTCCGCTATGCCCGAGGGCTACGTCCAGGAGCGCACCATCTTCTTCAAGGACGACGG
CAACTACAAGACCCGCGCTGAGGTCAAGTTCGAGGGCGACACCCTCGTCAACCGCATCGAGCTC
AAGGGCATCGACTTCAAGGAGGACGGCAACATCCTCGGCCACAAGCTCGAGTACAACTACAACT
CCCACAACGTCTACATCATGGCTGACAAGCAGAAGAACGGCATCAAGGTCAACTTCAAGATCCG
CCACAACATCGAGGACGGCTCCGTCCAGCTCGCTGACCACTACCAGCAGAACACCCCCATCGGC
GACGGCCCCGTCCTCCTCCCCGACAACCACTACCTCTCCTACCAGTCCGCTCTCTCCAAGGACC
CCAACGAGAAGCGCGACCACATGGTCCTCCTCGAGTTCGTCACCGCTGCTGGCATCACCCTCGG
CATGGACGAGCTCTACAAGTAACATATG

FIG. 5E pCT2*Ng*

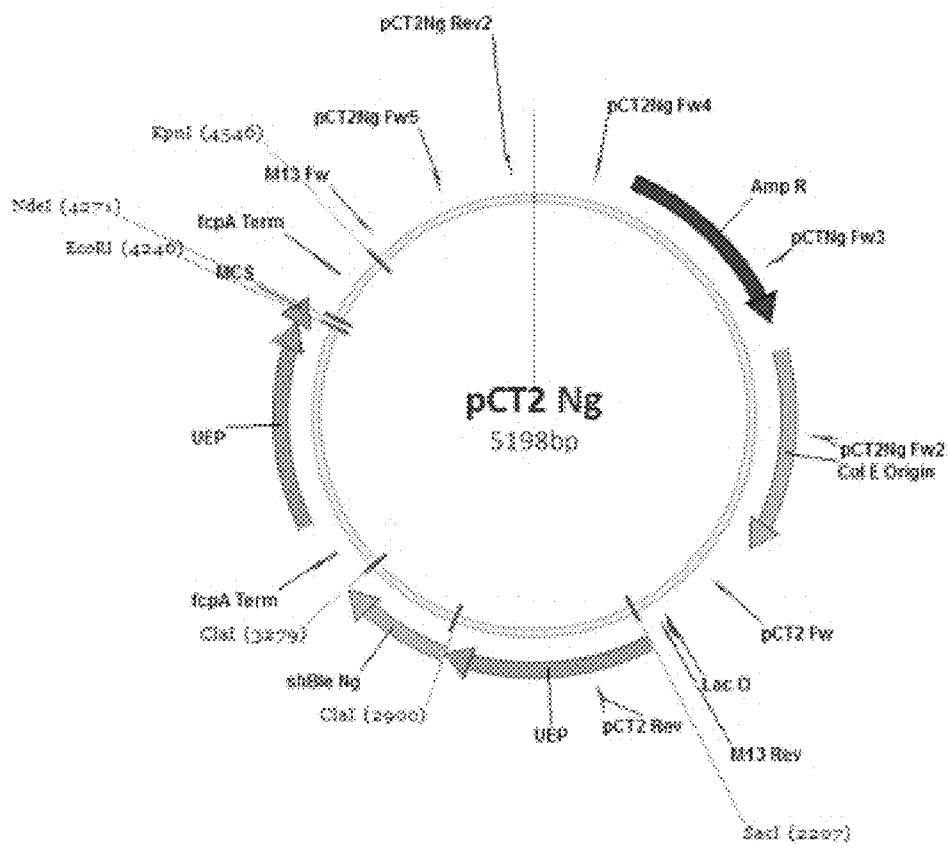

pCT56 pCT59

FIG. 6A
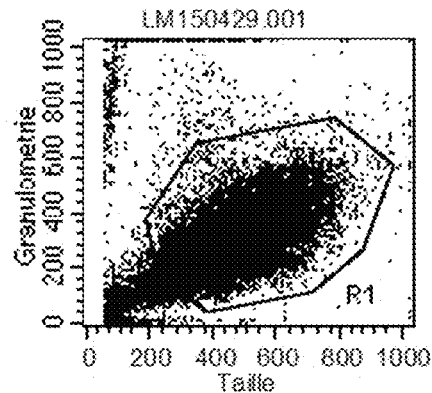
Serie pCT55
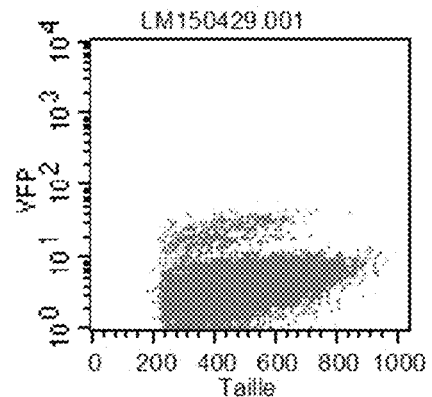
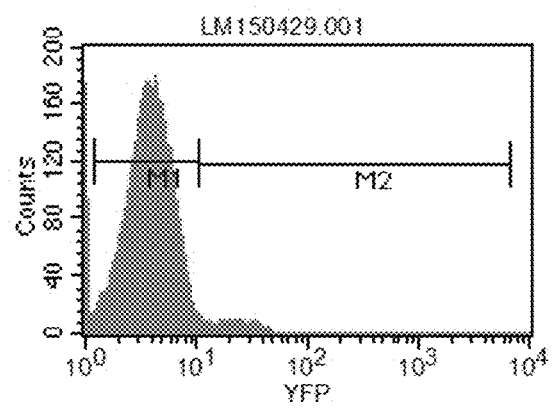
FIG. 6B
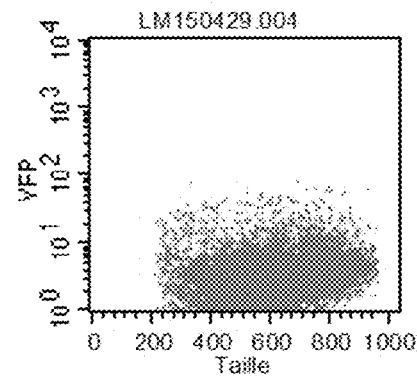
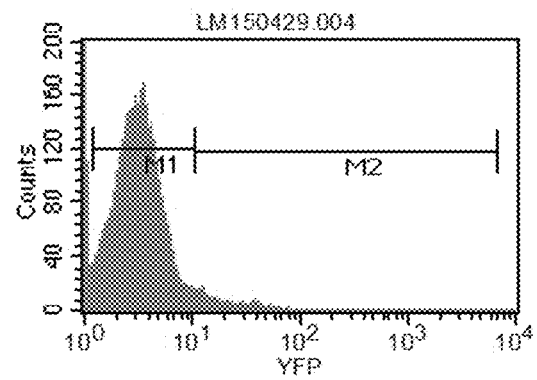

FIG. 7A
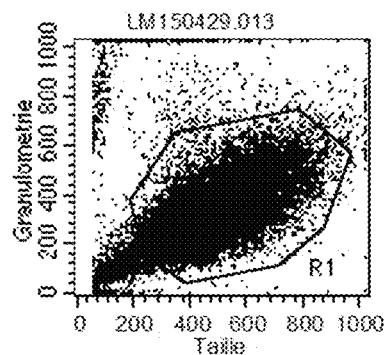
Serie pCT56
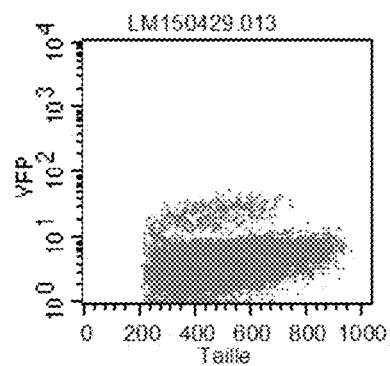
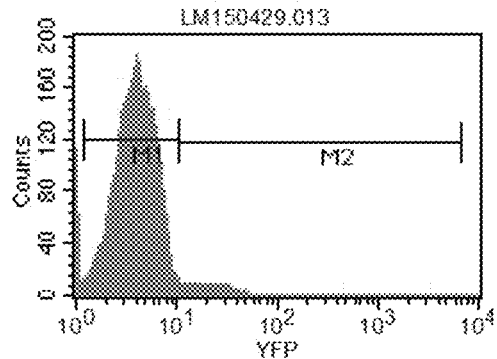
FIG. 7B
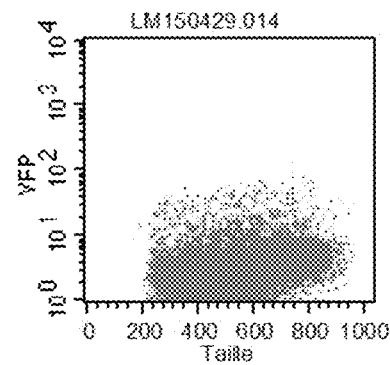
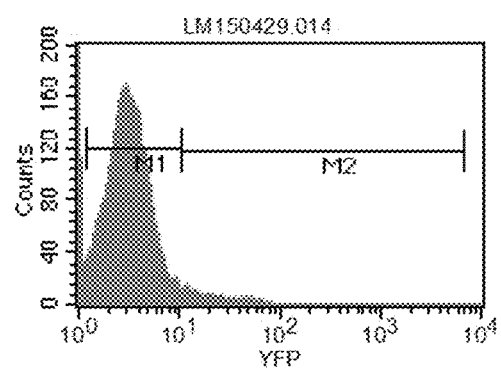

FIG. 7C
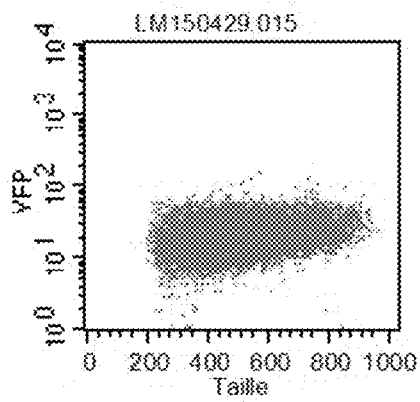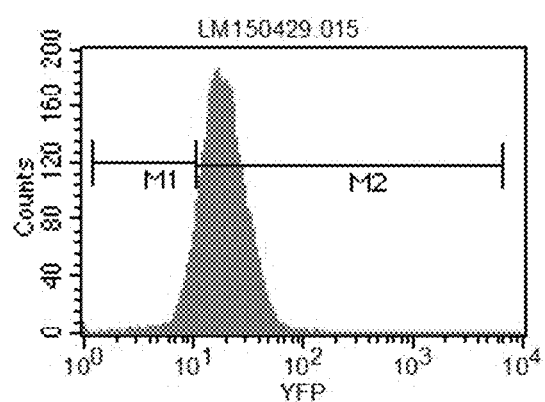

FIG. 8A
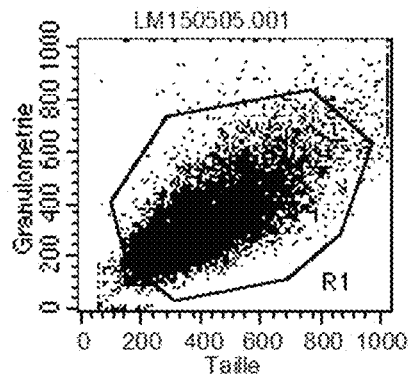
Serie pCT59
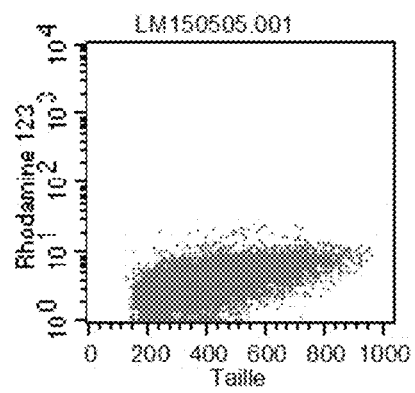
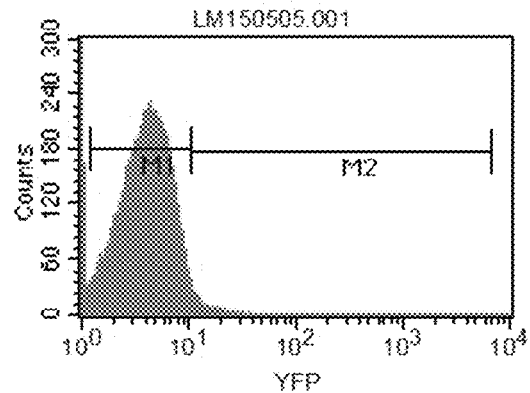
FIG. 8B
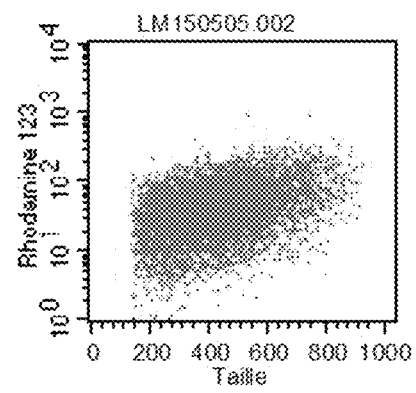
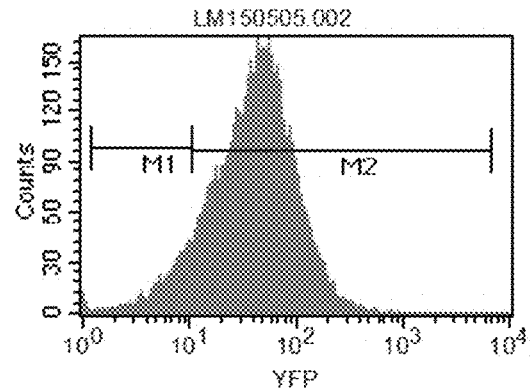

CHLOROPLAST TARGETING PEPTIDE SEQUENCE DERIVED FROM NANNOCHLOROPSIS PHOSPHORIBULOKINASE AND METHODS FOR USE

CROSS-REFERENCE TO RELATED APPLICATIONS

This application claims the benefit of PCT/EP2017/081451 filed Dec. 5, 2017, which claims priority from EP 16290225.8 filed Dec. 5, 2016, which are incorporated herein by reference in their entireties for all purposes.

SEQUENCE LISTING

The instant application contains a Sequence Listing which has been submitted in ASCII format and is hereby incorporated by reference in its entirety. Said ASCII copy, created on Jan. 21, 2021, is named BIO16-013_Sequence_Listing.txt and is 39,055 bytes in size.

TECHNICAL FIELD

The application generally relates to the field of genetic engineering, more particularly to genetic engineering of microalgae, in particular to target nuclear-encoded recombinant proteins to the chloroplast.

BACKGROUND

Microalgae are increasingly being used in industry for the biosynthesis of high-value products such as lipid products. Their ability to accumulate large amounts of lipids in the form of triacylglycerol (TAG), in particular when depriving nitrogen from their culture medium, has triggered their exploitation as host for fatty acid production, e.g. for biofuel production, for chemical applications or in food industry.

Microalgae can also be used as very efficient producing tools for heterologous proteins such as therapeutic proteins and industrial enzymes. Plastids are ideal subcellular hosts for storage of recombinant proteins as compared to the cytoplasm since adverse effects due to over-accumulation can be avoided and the recombinant proteins are protected from proteolytic degradation.

The insertion of transgenes into the plastid genome has proven to be an effective alternative to nuclear transformation for the production of recombinant proteins in plants (De Marchis et al. 2012 Plant Physiol. 160:571-581). In algae, it has been documented for the green alga *Chlamydomonas reinhardtii* (Muto et al. 2009 BMC Biotechnol. 9:26), the red alga *Porphyridium* sp. (Lapidot et al. 2002 Plant Physiol. 129:7-12), the euglenoid *Euglena gracilis* (Doetsch et al. 2001 Curr Genet. 39:49-60) and the diatom *Phaeodactylum tricornutum* (Xie et al. 2014 Mar Biotechnol (NY). 16:538-46). But for some algae, including *Nannochloropsis* species, chloroplast transformation has not been reported yet, and biotechnological applications are limited to nuclear transformation in these organisms. The nuclear-encoded recombinant proteins need then be targeted to the chloroplast. Microalgae harbor a unique plastid surrounded by four membranes, with the outermost membrane being interconnected with the endoplasmatic reticulum. To translocate across the multiple membranes of the microalgal plastids, host-encoded chloroplast proteins require a bipartite targeting sequence (BTS), with the N-terminal domain functioning as an ER signal sequence (Bhaya and Grossman 1991 Mol Gen Genet. 229:400-4) and the C-terminus acting as a transit peptide-like domain (Lang et al. 1998 J Biol Chem. 273:30973-8). Heterologous plastid pre-sequences are able to direct fluorescent markers into the plastids of cryptophytes, dinoflagellates and diatoms, stressing similarities in plastid protein import machinery across different phyla (Gruber et al. 2007 Plant Mol Biol. 64:519-30). These BTS, however, are highly variable with respect to their amino acid sequence, but a conserved "ASA-FAP" motif was observed in the BTS of diatoms and cryptophytes (Gruber et al. 2007). So far, only few BTS sequences of nuclear-encoded plastid proteins of chromophytic algae have been published, with one example in *Nannochloropsis* (Moog et al. 2015. Protist 166:161-71).

Besides promoting chloroplast localization in vivo, however, nothing is still known about the features that these BTS carry with respect to their effect on protein stability and responses to nutrient conditions.

Accordingly, there is a need for systems and methods for chloroplast targeting of nuclear-encoded recombinant proteins in microalgae, preferably which allow robust protein production under different culture conditions.

SUMMARY OF THE INVENTION

The present invention is based, at least in part, on the identification of new bipartite targeting sequences (BTS), such as from the phosphoribulokinase (PRK) of *N. gaditana*. This BTS was found to efficiently target nuclear-encoded recombinant proteins to the chloroplast in a host cell, and to promote robust accumulation of the recombinant proteins in the chloroplast. Moreover, it was determined that this chloroplast targeting was efficient under different nutrient conditions, including nitrogen starvation. Furthermore, protein expression was found to be uniform in host cells, allowing for reproducible genome engineering, such as for microalgae.

Accordingly, compositions and methods for chloroplast targeting of a nuclear-encoded proteins of interest are provided. More particularly, these compositions and methods are suitable for use in microalgae. Exemplary compositions comprise one or more expression cassettes comprising a nucleotide sequence encoding a chloroplast targeting peptide according to the invention operably linked to a nucleotide sequence encoding a protein of interest. The invention further provides vectors comprising the expression cassettes, and host cells, in particular microalgae, having such expression cassettes stably incorporated or transiently expressed into their nuclear genomes. Methods are also provided for production of a protein of interest in a microalgal cell. Also provided herein are methods for modulating chloroplast pathways.

The present invention is in particular captured by any one or any combination of one or more of the below numbered aspects and embodiments (i) to (xv) wherein:

(i) An isolated nucleic acid comprising a nucleotide sequence showing at least 70% sequence identity to SEQ ID NO: 9, wherein said nucleotide sequence encodes a chloroplast targeting peptide.

(ii) A nucleic acid expression cassette comprising a nucleotide sequence encoding a chloroplast targeting peptide operably linked to a nucleotide sequence encoding a protein of interest, wherein the chloroplast targeting peptide comprises the bipartite targeting sequence (BTS) of the phoshoribulokinase (PRK) of *Nannochloropsis gaditana* (NgPRK BTS) of SEQ ID NO: 8, and wherein the expression cassette ensures expression of the coding sequences in the nucleus of a host cell transformed with said expression cassette.

(iii) The expression cassette according to (ii), further comprising a promoter and a terminator operably linked to the nucleotide sequences encoding the chloroplast targeting peptide and the protein of interest.

(iv) The expression cassette according to any one of (ii) or (iii), wherein the protein of interest is a protein which is not said *Nannochloropsis gaditana* PRK, more particularly which is heterologous to *Nannochloropsis gaditana*.

(v) The expression cassette according to any one of (ii) to (iv), wherein the protein of interest is an enzyme or a modulator of an enzyme which can ensure a biochemical reaction or pathway in the chloroplast.

(vi) The expression cassette according to (v), wherein the protein of interest is an enzyme or a modulator of an enzyme involved in lipid biosynthesis such as TAG biosynthesis and storage, and fatty acid biosynthesis, or involved in chrysolaminarin or starch accumulation.

(vii) The expression cassette according to any one of (ii) to (iv), wherein the protein of interest is selected from the group comprising a chloroplast transporter, a protein of transcription or translation machinery, a transcription factors/enhancer/silencer, a nuclease, and a chaperone.

(viii) A vector comprising the expression cassette according to any one of (ii) to (vii).

(ix) A recombinant host cell which has been transformed with the expression cassette according to any one of (ii) to (vii) or the vector according to (viii), wherein said host cell is a microalga.

(x) The host cell according to (ix), wherein said microalga is a heterokont microalga, preferably selected from the group comprising *Nannochloropsis* and *Phaeodactylum* species.

(xi) The host cell according to (ix) or (x), wherein said microalga is the diatom *Nannochloropsis gaditana*.

(xii) A method for producing a protein of interest in the chloroplast of a microalga, said method comprising:
culturing a recombinant microalga that has been transformed with a nucleic acid comprising a nucleotide sequence encoding a chloroplast targeting peptide operably linked to a nucleotide sequence encoding the protein of interest, wherein the chloroplast targeting peptide comprises the bipartite targeting sequence (BTS) of the phoshoribulokinase (PRK) of *Nannochloropsis gaditana* (NgPRK BTS) of SEQ ID NO: 8.

(xiii) The method according to (xii) further comprising the steps of:
harvesting the chloroplast from the microalga; and
purifying the protein of interest from the chloroplast.

(xiv) The method according to (xii) or (xiii), wherein the recombinant microalga is cultured under conditions of nitrogen depletion.

(xv) Use of the recombinant host cell according to any one of (ix) to (xi) for introducing or modulating a biochemical reaction or a pathway in the chloroplast, wherein the protein of interest in said recombinant host cell is an enzyme or a modulator of an enzyme involved in said biochemical reaction or pathway.

BRIEF DESCRIPTION OF THE FIGURES

The teaching of the application is illustrated by the following Figures which are to be considered as illustrative only and do not in any way limit the scope of the claims.

FIG. 1: (A) Gene sequence of *Nannochloropsis gaditana* phosphoribulokinase (NgPRK) (SEQ ID NO:1). The coding sequence is underlined. (B) In silico protein sequence of NgPRK (SEQ ID NO:2). The "AF" motif is underlined.

FIG. 2: Prediction of a signal peptide sequence in the in silico protein sequence of NgPRK by SignalP.

FIG. 4: Secondary structure prediction of the in silico protein sequence of NgPRK by CFSSP (http://www.biogem.org/tool/chou-fasman/). The identified BTS is underlined (SEQ ID NO: 8).

FIG. 7: Representative FACS analysis of wild-type *N. gaditana* (A, Sample ID: WT), and negative (B, Sample ID: 56.1) and positive (C, Sample ID:56.2) pCT56 clones. eYFP-expressing cells were gated in the M2 part of the graph, whereas cells gated to the M1 were considered negative (see WT as a reference). M2-gated cutoff was chosen at 10% for identifying positive clones.

FIG. 8: Representative FACS analysis of wild-type *N. gaditana* (A, Sample ID: WT), and a positive (B, Sample ID: 59.10) pCT59 clone that expresses eYFP in the cytosol. eYFP-expressing cells were gated in the M2 part of the graph, whereas cells gated to the M1 were considered negative (see WT as a reference). M2-gated cutoff was chosen at 10% for identifying positive clones.

DETAILED DESCRIPTION OF THE INVENTION

Figure 3F:
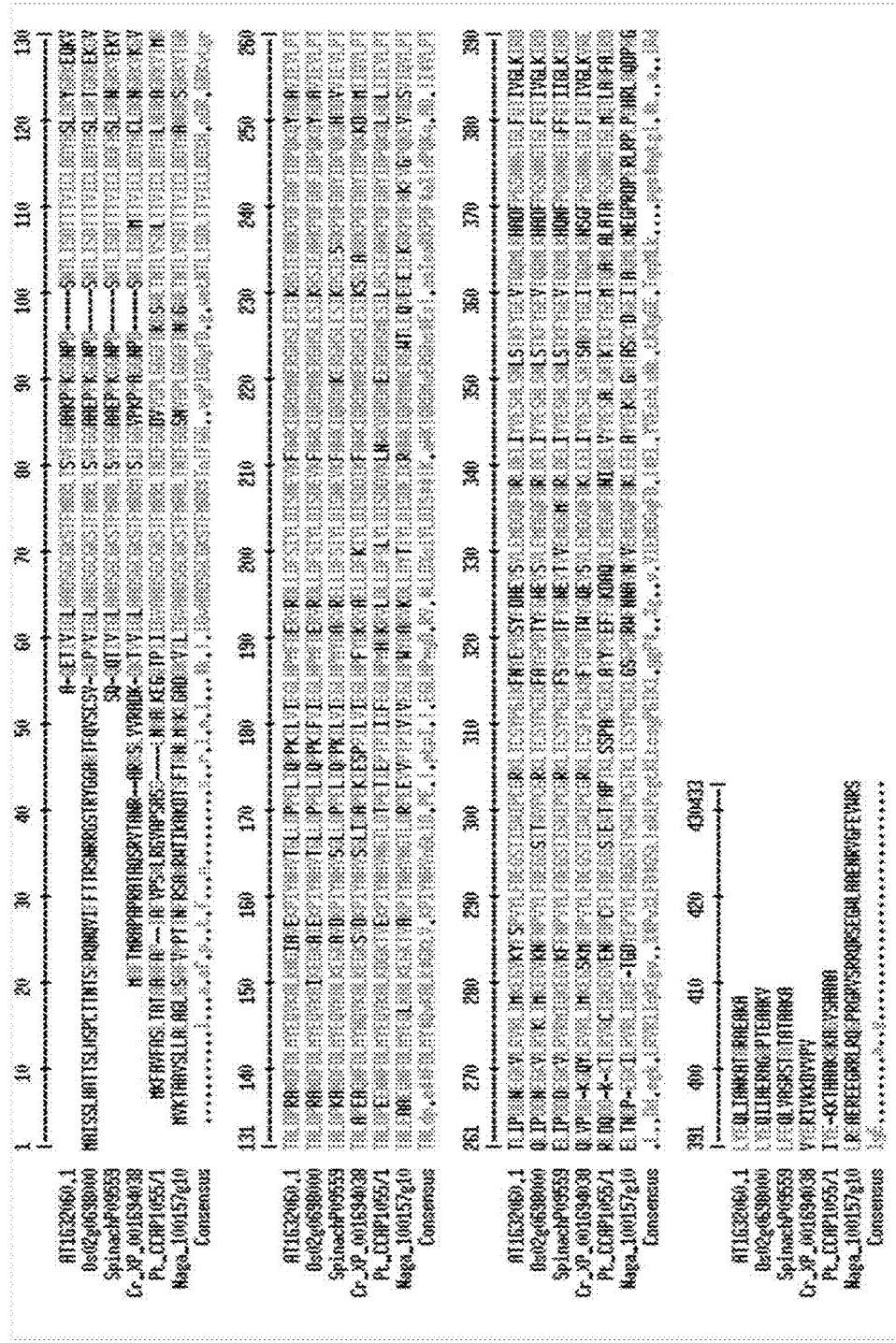
FIG. 3: Protein sequences of phosphoribulokinases (PRKs) of *Arabidopsis thaliana* (AT1G32060.1, SEQ ID NO: 3) (A), *Spinacea oleracea* (Spinach_P09559, SEQ ID NO:4) (B), *Phaeodactylum tricornutum* (Pt_CCAP1055/1, SEQ ID NO:5) (C), *Chlamydomonas reinhardtii* (Cr_XP_001694038, SEQ ID NO:6) (D), *Oryza sativa* (Os02g0698000, SEQ ID NO:7) (E). Raw protein sequences are shown; experimentally characterized transit peptides are underlined. (F) Multisequence alignment of different plant and algal PRK.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. Where reference is made to embodiments as comprising certain elements or steps, this encompasses also embodiments which consist essentially of the recited elements or steps.

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

All documents cited in the present specification are hereby incorporated by reference in their entirety.

The term "microalga" or "microalgae" (plural) as used herein refers to microscopic alga(e). "Microalgae" encompass, without limitation, organisms within (i) several eukaryotic phyla, including the Rhodophyta (red algae), Chlorophyta (green algae), Dinoflagellata, Haptophyta, (ii) several classes from the eukaryotic phylum Heterokontophyta, and (iii) the prokaryotic phylum Cyanobacteria (blue-green algae).

The term "heterokonts" or "stramenopiles" refer to the microalgae within the eukaryotic phylum Heterokontophyta or Stramenopila which includes, without limitation, the classes Bacillariophycea (diatoms), Eustigmatophycea, Phaeophyceae (brown algae), Xanthophyceae (yellow-green algae) and Chrysophyceae (golden algae).

The term "transformation" as used herein refers to introducing a recombinant nucleic acid into an organism in such a way that that the nucleic acid is replicable, either as an extrachromosomal element or by chromosomal integration.

The terms "genetically engineered" or "genetically modified" or "recombinant" as used herein with reference to a host cell, in particular a microalga or plant cell, denote a non-naturally occurring host cell, as well as its recombinant progeny, that has at least one genetic alteration not found in a naturally occurring strain of the referenced species, including wild-type strains of the referenced species. Such genetic modification is typically achieved by technical means (i.e. non-naturally) through human intervention and may include, e.g., the introduction of an exogenous nucleic acid and/or the modification, over-expression, or deletion of an endogenous nucleic acid.

The term "exogenous" or "foreign" as used herein is intended to mean that the referenced molecule, in particular nucleic acid, is not naturally present in the host cell. The term "endogenous" or "native" as used herein denotes that the referenced molecule, in particular nucleic acid, is naturally present in the host cell.

By "recombinant nucleic acid" when referring to a nucleic acid in a recombinant host cell, is meant that at least part of said nucleic acid is not naturally present in the host cell in the same genomic location. For instance a recombinant nucleic acid can comprise a coding sequence naturally occurring in the host cell under control of an exogenous promotor, or a recombinant nucleic acid can comprise an exogenous coding sequence under the control of an endogenous promoter. A recombinant host cell similarly refers to a host cell comprising a recombinant nucleic acid, i.e. a nucleic acid which does not naturally occur in that host cell in that genomic location.

As used herein, the term 'nucleic acid expression cassette' refers to nucleic acid molecules that include one or more transcriptional control elements (such as, but not limited to promoters and/or enhancers, and transcription terminators) that direct expression of a (trans)gene of interest in a host cell. Typically, these contain a transgene, although it is also envisaged that a nucleic acid expression cassette is used to direct expression of an endogenous gene in a host cell into which the nucleic acid cassette is inserted.

The term 'operably linked' as used herein refers to the arrangement of various nucleic acid molecule elements relative to each such that the elements are functionally connected and are able to interact with each other. Such elements may include, without limitation, a promoter and/or an enhancer, a transcription terminator, and a coding sequence of a gene of interest to be expressed (i.e., the transgene). The nucleic acid sequence elements, when properly oriented or operably linked, act together to modulate the activity of one another, and ultimately may affect the level of expression of the transgene. By modulate is meant increasing, decreasing, or maintaining the level of activity of a particular element. The position of each element relative to other elements may be expressed in terms of the 5' terminus and the 3' terminus of each element, and the distance between any particular elements may be referenced by the number of intervening nucleotides, or base pairs, between the elements. As understood by the skilled person, operably linked implies functional activity, and is not necessarily related to a natural positional link.

By "encoding" is meant that a nucleic acid sequence or part(s) thereof corresponds, by virtue of the genetic code of an organism in question, to a particular amino acid sequence, e.g., the amino acid sequence of a desired polypeptide or protein. By means of example, nucleic acids "encoding" a particular polypeptide or protein may encompass genomic, hnRNA, pre-mRNA, mRNA, cDNA, recombinant or synthetic nucleic acids.

A nucleic acid encoding a particular peptide, polypeptide or protein will comprise an open reading frame (ORF) encoding said peptide, polypeptide or protein. An "open reading frame" or "ORF" refers to a succession of coding nucleotide triplets (codons) starting with a translation initiation codon and closing with a translation termination codon known per se, and not containing any internal in-frame translation termination codon, and potentially capable of encoding a peptide, polypeptide or protein. Hence, the term may be synonymous with "coding sequence" as used in the art.

As used in the application, the term "promoter" refers to a nucleic acid sequence capable of binding RNA polymerase and initiating the transcription of one or more nucleic acid coding sequences to which it is operably linked. A promoter is usually located near the transcription start site of a (trans)gene on the same strand and upstream on the nucleotide coding sequence (5' in the sense strand). A promoter may function alone to regulate transcription or may be further regulated by one or more regulatory sequences (e.g. enhancers or silencers).

The term "transcription termination sequence" encompasses a control sequence at the end of a transcriptional unit, which signals 3' processing and termination of transcription.

The term "enhancer" as used herein refers to a nucleotide sequence that acts to increase the transcription activity of a promoter compared to that resulting from the promoter in the absence of the enhancer.

As used herein, the term "selectable marker gene" includes any gene, which confers a phenotype on a host cell in which it is expressed to facilitate the identification and/or selection of host cells which are transfected or transformed with a transgene.

By "nucleic acid" is meant oligomers and polymers of any length composed essentially of nucleotides, e.g., deoxyribonucleotides and/or ribonucleotides. Nucleic acids can comprise purine and/or pyrimidine bases and/or other natural (e.g., xanthine, inosine, hypoxanthine), chemically or biochemically modified (e.g., methylated), non-natural, or derivatised nucleotide bases. The backbone of nucleic acids can comprise sugars and phosphate groups, as can typically be found in RNA or DNA, and/or one or more modified or substituted sugars and/or one or more modified or substituted phosphate groups. Modifications of phosphate groups or sugars may be introduced to improve stability, resistance to enzymatic degradation, or some other useful property. A "nucleic acid" can be for example double-stranded, partly double stranded, or single-stranded. Where single-stranded, the nucleic acid can be the sense strand or the antisense strand. The "nucleic acid" can be circular or linear. The term "nucleic acid" as used herein preferably encompasses DNA and RNA, specifically including genomic, hnRNA, pre-mRNA, mRNA, cDNA, recombinant or synthetic nucleic acids, including vectors.

The terms "polypeptide" and "protein" are used interchangeably herein and generally refer to a polymer of amino acid residues linked by peptide bonds, and are not limited to a minimum length of the product. Thus, peptides, oligopeptides, polypeptides, dimers (hetero- and homo-), multimers (hetero- and homo-), and the like, are included within the definition. Both full-length proteins and fragments thereof are encompassed by the definition. The terms also include post-expression modifications of the polypeptide, for example, glycosylation, acetylation, phosphorylation, etc. Furthermore, for purposes of the present invention, the terms also refer to such when including modifications, such as deletions, additions and substitutions (e.g., conservative in nature), to the sequence of a native protein or polypeptide.

The term "variant", when used in connection to a protein, for example as in "a variant of protein X", refers to a protein that is altered in its sequence compared to protein X, but that retains the activity of protein X (i.e. a functional variant). Preferably, such variant would show at least 80%, more preferably at least 85%, even more preferably at least 90%, and yet more preferably at least 95% such as at least 96%, at least 97%, at least 98% or at least 99% sequence identity to the reference protein, preferably calculated over the entire length of the sequence. The sequence changes may be naturally occurring, for example, due to the degeneracy of the genetic code, or may be introduced artificially, for example by targeted mutagenesis of the respective sequence. Such techniques are well known to the skilled person.

As used herein, the terms "identity" and "identical" and the like are used interchangeably with the terms "homology" and "homologues" and the like herein and refer to the sequence similarity between two polymeric molecules, e.g., between two nucleic acid molecules or polypeptides. Methods for comparing sequences and determining sequence identity are well known in the art. By means of example, percentage of sequence identity refers to a percentage of identical nucleic acids or amino acids between two sequences after alignment of these sequences. Alignments and percentages of identity can be performed and calculated with various different programs and algorithms known in the art. Preferred alignment algorithms include BLAST (Altschul, 1990; available for instance at the NCBI website) and Clustal (reviewed in Chenna, 2003; available for instance at the EBI website). Preferably, BLAST is used to calculate the percentage of identity between two sequences, such as the "Blast 2 sequences" algorithm described by Tatusova and Madden 1999 (FEMS Microbiol Lett 174: 247-250), for example using the published default settings or other suitable settings (such as, e.g., for the BLASTN algorithm: cost to open a gap=5, cost to extend a gap=2, penalty for a mismatch=-2, reward for a match=1, gap x_dropoff=50, expectation value=10.0, word size=28; or for the BLASTP algorithm: matrix=Blosum62, cost to open a gap=11, cost to extend a gap=1, expectation value=10.0, word size=3).

The present application generally relates to genetic engineering, more particularly to methods of targeting a recombinant protein to the chloroplast. In particular embodiments, methods and tools are provided for the genetic engineering of microalgae, more particularly to chloroplast targeting of recombinant proteins in microalgae.

Chloroplast Targeting Peptides

Chloroplasts (also referred to as plastids herein) are organelles found in plant cells and algae that conduct photosynthesis. Heterokonts contain a complex plastid, which evolved via secondary endosymbiosis. During this process, a red algal-like cell was engulfed by an eukaryotic host and subsequently reduced to an organelle surrounded by four membranes. The outermost membrane is connected to the nuclear envelope and endoplasmic reticulum (ER) membrane and is called the chloroplast ER (cER) membrane. The former plasma membrane and the cytoplasm of the endosymbiont gave rise to the second outermost plastid membrane and the periplastidal compartment (PPC), respectively. The PPC surrounds the original primary plastid which itself possesses two envelope membranes.

Targeting proteins into the complex plastid (i.e. chloroplast targeting) typically requires at least an N-terminal signal peptide (SP) for cER import and a transit peptide-like sequence (TPL) for further transport across the PPM and beyond. Both sequences build up a bipartite targeting sequence (BTS), which is present at the N-terminus of host-encoded chloroplast proteins.

The present inventors have identified a sequence of a *Nannochloropsis gaditana* plastid protein which is capable of targeting a heterologous protein to the chloroplast. In particular embodiments, the application thus provides the BTS of the phosphoribulokinase (PRK) of *Nannochloropsis gaditana* (NgPRK), which is capable of targeting a heterologous protein to the chloroplast. An exemplary amino acid sequence of NgPRK BTS is set forth in SEQ ID NO:8. The NgPRK BTS is encoded by the nucleotide sequence of SEQ ID NO:9 or variants thereof.

In particular embodiments, the identified NgPRK BTS was found to be useful for targeting a polypeptide linked to it to the chloroplast of a microalga.

In an aspect, the invention provides an isolated nucleic acid comprising the nucleotide sequence of SEQ ID NO:9 or a variant thereof.

In embodiments, the variants include nucleotide substitutions, deletions, and/or insertions of one or more nucleotides of SEQ ID NO:9 without altering the ability of the encoded peptide to target a protein linked to it to the chloroplast. Variant nucleotide sequences may for instance be codon-optimized sequences to ensure recombinant expression in a host cell of choice. For instance, nucleotide sequences having at least about 70%, preferably at least about 80%, more preferably at least about 85%, 90% or 95%, even more preferably at least about 96%, 97%, 98% or 99% sequence identity to SEQ ID NO:9 and encoding a chloroplast targeting peptide are envisaged herein. More particularly, the variant nucleotide sequence encodes a protein having an amino acid sequence of SEQ ID NO:8 or an amino acid sequence of at least 95% sequence identity with SEQ ID NO:8.

Variants (or mutants) of sequences identified herein can be naturally occurring or they can be man-made e.g. using genetic engineering techniques. Such techniques are well known in the art and include, for example but without limitation, site directed mutagenesis, random chemical mutagenesis, and standard cloning techniques.

Provided herein is a bipartite targeting sequence (BTS) from *Nannochloropsis gaditana* encoded by SEQ ID NO:9 and variants of the NgPRK BTS. It is understood that the BTS variants described herein may have conservative or non-essential amino acid substitutions, as compared to the wild-type BTS, which do not have a substantial effect on the BTS function. Whether or not a particular substitution will be tolerated (i.e., will not adversely affect desired biological properties) can be determined as described in Bowie et al. (1990) (Science 247:1306 1310). A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). BRS variants intended herein may have one or more amino acid substitutions, preferably conservative amino acid substitutions, of SEQ ID NO:8. The BTS variants may have an amino acid sequence substantially identical to SEQ ID NO:8 or they may have an amino acid sequence having at least about 70%, preferably at least about 80%, more preferably at least about 85%, 90% or 95%, even more preferably at least about 96%, 97%, 98% or 99% sequence identity to SEQ ID NO:8.

Other BTS variants include functional or active fragments comprising at least about 30, 35, 40, 45, 46, 47, 48, 49, 50 or 51 consecutive amino acids, and which retain the same biological function as NgPRK BTS (e.g. retain chloroplast targeting of a nuclear-encoded protein linked to it).

It is to be understood that the BTS variants envisaged herein are functional or (biologically) active variants that retain the biological activity of NgPRK BTS, that is, retaining chloroplast targeting activity (i.e. facilitating translocation of a protein linked to it to the chloroplast). By "retaining chloroplast targeting activity" is meant that the variant BTS will direct the translocation of at least about 50%; preferably at least about 60% or at least about 70%, more preferably at least about 80% of the protein linked to it. Methods for measuring chloroplast targeting activity are well known in the art and include, for example, but without limitation, operably linking a reporter gene such as green fluorescent protein (GTP) to the BTS encoding nucleotide sequence. This construct is placed under the control of a suitable promoter, ligated into a vector, and transformed into a microalgal cell. Following an adequate period of time for expression and localization into the chloroplast, the reporter is localized by means well known in the art.

Expression Cassettes

A chloroplast targeting peptide-encoding nucleotide sequence as described herein may be provided in a nucleic acid expression cassette operably linked to a nucleotide sequence encoding a protein of interest, which expression cassette allows it to be expressed in a host cell. After expression the BTS will translocate the polypeptide of interest to the chloroplast.

A nucleic acid expression cassette envisaged herein thus comprises a nucleotide sequence encoding a chloroplast targeting peptide as described herein operably linked to a nucleotide sequence encoding a protein of interest. In particular, the present invention provides a nucleic acid expression cassette comprising a nucleotide sequence encoding NgPRK BTS operably linked to a nucleotide sequence encoding a protein of interest. More particularly, the present invention provides a nucleic acid expression cassette comprising a nucleotide sequence of SEQ ID NO:9 or a variant thereof, operably linked to a nucleotide sequence encoding a protein of interest.

The chloroplast targeting peptide-encoding nucleotide sequence and the nucleotide sequence encoding the protein of interest may be contiguous and in the same reading frame, or they may be separated from one another by a nucleotide sequence encoding one or more "linker" amino acids. The length of this linker may vary from a small peptide (e.g. 2, 3, 4 or more amino acids) to a protein of polypeptide such as a reporter protein.

The protein of interest may be any protein. In particular embodiments, the protein of interest is not the natural *N. gaditana* PRK. In further particular embodiments, the protein of interest is not a protein from *N. gaditana*. Indeed, the present inventors have shown that the BTS sequence of the *N. gaditana* PRK is able to translocate a reporter protein to the chloroplast. The protein of interest may be of animal origin, preferably of mammalian origin, more preferably of human origin. Alternatively, the protein can be a synthetic protein.

The protein of interest may thus be a heterologous protein. The term "heterologous" is generally used herein with reference to a protein or nucleic acid sequence means an amino acid or polynucleotide sequence that does not naturally occur in the host cell into which it is to be introduced. The term "heterologous" when referring to one amino acid (or nucleic acid sequence) with respect to another amino acid sequence protein (or nucleic acid sequence) can also be used to refer to the fact that the two amino acid sequences (or nucleic acid sequence) do not naturally occur together in the same a host cell. For instance, as detailed above, in the context of the present invention fusion proteins of the *N. gaditana* BTS sequence with heterologous proteins, i.e. proteins which do not naturally occur in *N. gaditana* are envisaged.

Said protein of interest may for instance be a protein used for therapeutic purposes, including, without limitation, antibodies or antibody fragments.

The protein of interest may be an enzyme, such as an enzyme involved in a biochemical reaction taking place in the chloroplast or a chloroplast pathway. A "chloroplast pathway" as used herein refers to a pathway which naturally takes place in the chloroplast. In alternative embodiments, the enzyme may be involved in a biochemical reaction or pathway which does not naturally take place in the chloroplast of the host cell, and the purpose is to ensure this biochemical reaction or pathway in the chloroplast. Examples of pathways which in some micro-organisms take place in the chloroplast are lipid biosynthesis pathways such as fatty acid synthesis pathways and TAG synthesis, and chrysolaminarin or starch accumulation. The protein of interest may also be a modulator such as an inducer or inhibitor of an enzyme as taught herein. Indeed, nuclear expression and chloroplast translocation of enzymes or modulators of enzymes as taught herein is of particular interest in the context of introducing or modulating biochemical reactions and pathways taking place in the chloroplast of a host cell. For example, the proteins of interest may be enzymes or modulators of enzymes involved in the fatty acid pathway.

The protein of interest may also be a chloroplast transporter, such as a carrier protein.

Further, non-limiting, examples of proteins of interest include proteins of transcription or translation machinery, transcription factors/enhancers/silencers, endogenous or engineered nucleases, chaperones, etc.

The nucleic acid expression cassettes disclosed herein further comprises transcription regulatory elements to ensure expression of the coding sequences in a host cell. In particular embodiments, the expression cassette comprises regulatory elements to ensure expression of a coding sequence in a microalga. In preferred embodiments, the cassette ensures expression in the nucleus of the host cell.

Transcription regulatory elements include, without limitation, promoters, enhancers, and terminators. The nature of the host cell will determine the nature of the regulatory elements of the expression cassette. For expression in microalgae, a promoter functional in microalgae can be operably linked to the nucleotide sequences encoding the chloroplast targeting peptide and the protein of interest. Suitable promoters to direct expression in microalgae include, without limitation, those from *Chlamydomonas reinhardtii*, and from *Chlorella* species including *Chlorella vulgaris*, *Nannochloropsis* sp, *Phaeodactylum tricornutum*, *Thalassiosira* sp, *Dunaliella salina* and *Haematococcus pluvialis*. Non-limiting examples of suitable promoters are the Hsp70A promoter, the RbcS2 promoter and the beta-2-tubulin (TUB2) promoter from *Chlamydomonas reinhardtii*, the fucoxanthin chlorophyll a/b-binding protein (fcp) promoters, Histone 4 (H4) promoter from *Phaeodactylum tricornutum*, the Nitrate reductase (NR) promoter from *Thalassiosira*, and ubiquitin extension protein (UEP) from *Nannochloropsis* sp. The promoter may be an endogenous (to the host cell) nuclear promoter or an exogenous promoter. In certain embodiments, the promoter is endogenous to *N. gaditana* or an exogenous promoter, in particular a promoter from another *Nannochloropsis* sp. In embodiments, the promoter in the expression cassettes envisaged herein is the ubiquitin extension protein (UEP) from *Nannochloropsis gaditana*.

In embodiments, the expression cassettes further comprise a transcription termination sequence or terminator. Any polyadenylation signal that directs the synthesis of a polyA tail is useful in the expression cassettes described herein, examples of those are well known to one of skill in the art. Exemplary polyadenylation signals include, but are not limited to, the polyadenylation signal derived from the Simian virus 40 (SV40) late gene, and the bovine growth hormone (BGH) polyadenylation signal, or the terminator region of the fucoxanthin chlorophyll a/b-binding protein (fcp) gene, such as the fcpA terminator. The terminator may be endogenous to the host cell or exogenous. In certain embodiments, the terminator is endogenous to *N. gaditana* or an exogenous terminator, in particular a terminator from another *Nannochloropsis* sp. In embodiments, the fcpA terminator is used in the expression cassettes envisaged herein.

Promoter and terminator sequences may be native to the host cell or exogenous to the host cell. Useful promoter and terminator sequences include those that are highly identical (i.e. having an identities score of 90% or more, preferably 95% or more, most preferably 99% or more) in their functional portions compared to the functional portions of promoter and terminator sequences, respectively, that are native to the host cell, particularly when the insertion of the recombinant nucleic acid is targeted at a specific site in the host (nuclear) genome. The use of native (to the host) promoters and terminators, together with their respective upstream and downstream flanking regions, can permit the targeted integration of the cassette into specific loci of the host (nuclear) genome.

Other sequences may be incorporated in the expression cassettes according to the invention. More particularly the inclusion of sequences which further increase the expression of the coding sequences or stabilize the transcription products (e.g. enhancers, introns) is envisaged. Enhancers are well known in the art and include, without limitation, the SV40 enhancer region and the 35S enhancer element.

The nucleic acid expression cassette described herein may further contain one or more nucleic acid coding sequences for a selectable marker gene as further described herein.

The nucleic acid expression cassette may further contain restriction sites e.g. for insertion in a vector.

Vector

The expression cassettes envisaged herein may be used as such, or typically, they may be part of (i.e. introduced into) a nucleic acid vector. Accordingly, a further aspect relates to a vector comprising a nucleic acid expression cassette envisaged herein.

In embodiments, the vectors disclosed herein further comprise an expression cassette comprising a selectable marker gene, such as an antibiotic resistance cassette, to allow selection of host cells that have been transformed. A selectable marker gene cassette typically includes a promoter and transcription terminator sequence, operatively linked to a selectable marker gene. Suitable markers may be selected from markers that confer antibiotic resistance, herbicide resistance, visual markers, or markers that complement auxotrophic deficiencies of a host cell, in particular a microalga. For example, the selection marker may confer resistance to an antibiotic such as hygromycin B (such as the hph gene), zeocin/phleomycin (such as the ble gene), kanamycin or G418 (such as the nptII or aphVIII genes), spectinomycin (such as the aadA gene), neomycin (such as the aphVIII gene), blasticidin (such as the bsd gene), nourseothricin (such as the natR gene), puromycin (such as pac gene) and paromomycin (such as the aphVIII gene). In other examples, the selection marker may confer resistance to a herbicide such as glyphosate (such as GAT gene), oxyfluorfen (such as protox/PPO gene) and norflurazon (such as PDS gene). Visual markers may also be used and include for example beta-glucuronidase (GUS), luciferase and fluorescent proteins such as Green Fluorescent Protein (GFP), Yellow Fluorescent protein, etc. Two prominent examples of auxotrophic deficiencies are the amino acid leucine deficiency (e.g. LEU2 gene) or uracil deficiency (e.g. URA3 gene). Cells that are orotidine-5'-phosphate decarboxylase negative (ura3−) cannot grow on media lacking uracil. Thus a functional URA3 gene can be used as a selection marker on a host cell having a uracil deficiency, and successful transformants can be selected on a medium lacking uracil. Only cells transformed with the functional URA3 gene are able to synthesize uracil and grow on such medium. If the wild-type strain does not have a uracil deficiency, an auxotrophic mutant having the deficiency must be made in order to use URA3 as a selection marker for the strain. Methods for accomplishing this are well known in the art.

The vectors disclosed herein may further include an origin of replication that is required for maintenance and/or replication in a specific cell type. One example is when a vector is required to be maintained in a host cell as an episomal genetic element (e.g. plasmid or cosmid molecule). Exemplary origins of replication include, but are not limited to the f1-ori, colE1 ori, and Gram+ bacteria origins of replication.

The vectors taught herein may further contain restriction sites of various types for linearization or fragmentation.

Numerous vectors are known to practitioners skilled in the art and any such vector may be used. Selection of an appropriate vector is a matter of choice. The vector may be a non-viral or viral vector. Non-viral vectors include but are not limited to plasmids, cationic lipids, liposomes, nanoparticles, PEG, PEI, etc. Viral vectors are derived from viruses including but not limited to: retrovirus, lentivirus, adeno-associated virus, adenovirus, herpesvirus, hepatitis virus or the like. Preferred vectors are vectors developed for microalgae such as the vector called pCT2Ng.

Construction of the vectors described herein containing or including the herein described expression cassettes, and optionally the selectable marker cassettes, and one or more of the above listed optional components employs standard ligation techniques. For example, isolated plasmids may be cleaved, tailored, and re-ligated in the form desired to generate the plasmids required.

Recombinant Host Cells

A further aspect relates to recombinant host cells that have been transformed with an expression cassette or a vector as described herein. Accordingly, disclosed herein are recombinant host cells comprising an exogenous nucleic acid comprising a nucleotide sequence encoding NgPRK BTS or a variant thereof operably linked to a nucleotide sequence encoding a protein of interest. In particular, disclosed herein are recombinant host cells comprising an exogenous nucleic acid comprising a nucleotide sequence of SEQ ID NO:9 or a variant thereof operably linked to a nucleotide sequence encoding a protein of interest. Advantageously, the NgPRK BTS was found to ensure uniform expression levels of the protein linked to it across the cell population, allowing for reproducible engineering of host cells.

Preferred host cells are microalgae.

Preferred microalgae are microalgae that harbor a chloroplast (i.e. photosynthesizing microalgae), including species from the phyla heterokonts, dinoflagellates, cryptophytes, haptophytes and chlorophytes. In embodiments, the microalgae are heterokont microalgae, including Eustigmatophytes such as *Nannochloropsis* ( ) species, *Phaeodactylum, Chaetoceros, Emiliana, Amphora, Anikstrodesmis, Fistulifera, Cyclotella, Cylindrotheca, Tribonema, Hematococcus, Isochrysis, Monochrysis, Monoraphidium, Navicula, Nitzschia, Tetraselmis, Thalassiosira*, and *Trichodesmium* species, brown algae such as *Macrocystis* species. In further embodiments, the microalga is an Eustigmatophyte, preferably a *Nannochloropsis* species, more preferably *Nannochloropsis gaditana*.

Also provided herein are methods for obtaining a genetically engineered or recombinant host cell as described herein, which method may comprise transforming a host cell with an expression cassette or a vector as taught herein above. The method may further comprise the step of selecting the host cells which have taken up the exogenous nucleic acids.

Methods used herein for transformation, in particular nuclear transformation, of the host cells are well known to a skilled person. For example, electroporation, chemical (such as calcium chloride- or lithium acetate-based) transformation methods, microparticles bombardment, glass beads, or viral- or Agrobacterium tumefaciens-mediated transformation methods as known in the art can be used for transformation of microalgae.

The expression cassettes or vectors disclosed herein may either be integrated into the nuclear genome of the host cell or they may be maintained in some form (such as a plasmid) extra chromosomally. A stably transformed host cell is one in which the exogenous nucleic acid has become integrated into a chromosome so that it is inherited by daughter cells through chromosome replication.

Successful transformants can be selected for in known manner, e.g. by taking advantage of the attributes contributed by the marker gene, or by other characteristics resulting from the introduced coding sequences (such as ability to translocate the encoded proteins to the chloroplast by conventional methods including immunocytochemistry and confocal microscopy). Screening can also be performed by PCR or Southern analysis to confirm that the desired insertions have taken place, to confirm copy number and to identify the point of integration of coding sequences into the host genome.

Uses and Methods

A further aspect relates to the use of the herein described expression cassettes and vectors for the nuclear expression and subsequent targeting of a protein of interest to the chloroplast in a host cell, in particular a microalga. The protein of interest preferably accumulates in the chloroplast (i.e. is stored in the chloroplast) or is functional in the chloroplast. In particular embodiments, the protein of interest is an enzyme which can ensure a biochemical reaction in a chloroplast. The methods may involve targeting other components involved in said biochemical reaction to the chloroplast.

A related aspect is directed to methods for the production of a protein of interest, which protein of interest preferably accumulates in the chloroplast and/or is functional in the chloroplast, using the recombinant host cells described herein. The protein of interest, which is linked to a BTS as described herein, is expressed in the nucleus of the host cell and then targeted to the chloroplast. Advantageously, the NgPRK BTS was found to allow for robust nuclear expression and accumulation in the chloroplast.

Accordingly, disclosed herein is a method for the production of a protein of interest, said method comprising culturing a host cell comprising an exogenous nucleic acid comprising a nucleotide sequence encoding a chloroplast targeting peptide comprising the NgPRK BTS, in particular the nucleotide sequence of SEQ ID NO:9, operably linked to a nucleotide sequence encoding the protein of interest. Preferably, the host cells are cultured under conditions suitable to ensure nuclear expression of the coding sequences in the host cell.

The method may further comprise a former step of transforming a host cell with the herein described expression cassettes or vectors as described elsewhere herein.

In certain embodiments, the protein of interest merely accumulates in the chloroplast, i.e. the protein of interest is stored in the chloroplast. Typically, these methods further involve the steps of harvesting the chloroplasts from the microalga and purifying the protein of interest from the chloroplasts. These methods are particularly useful for the production of heterologous proteins such as, without limitation, therapeutic proteins or industrial enzymes. The chloroplast advantageously protects the protein of interest against degradation and adverse effects due to over-accumulation can be avoided as compared to the cytoplasm.

The isolation of chloroplasts from the recombinant or transformed microalgae described herein may include, but is not limited to, the use of density gradient centrifugation.

Purification of the protein of interest can be carried out, for example, but without limitation, by chromatography. Alternatively, the protein of interest may be fused to an amino- or carboxy-terminal tag such as a histidine tag composed of six histidine residues for purification purposes.

In other embodiments of the method, the protein of interest is functional in the chloroplast. For example, the protein of interest may be an enzyme involved in a chloroplast pathway such as a fatty acid pathway or a pathway for the synthesis of triacylglycerol. By nuclear expression and chloroplast targeting of said enzyme, the chloroplast pathway can be modulated (e.g. stimulated or suppressed) resulting in a changed (e.g. increased or decreased) production of a biomolecule derived from said pathway, such as a biomolecule produced by said pathway. For example, to increase the production of a chloroplast biomolecule (i.e. a biomolecule derived from or produced by a pathway operative in the chloroplast), the host cell, in particular the microalga, may be transformed with an exogenous nucleic acid comprising a nucleotide sequence encoding a chloroplast targeting peptide comprising the NgPRK BTS of SEQ ID NO: 8 or a variant thereof, operably linked to a nucleotide sequence encoding said enzyme, and culturing the recombinant host cell. Accordingly, also disclosed herein is a method for modulating the production of a biomolecule of interest, said biomolecule being derived from, in particular produced in, a chloroplast pathway, said method comprising culturing a host cell comprising an exogenous nucleic acid comprising a nucleotide sequence encoding a chloroplast targeting peptide comprising the NgPRK BTS of SEQ ID NO: 8 or a variant thereof, operably linked to a nucleotide sequence encoding an enzyme involved in said chloroplast pathway.

In further examples, the protein of interest that is functional in the chloroplast may be a modulator such as an inducer or an inhibitor of an enzyme involved in a chloroplast pathway. The nuclear expression and targeting to the chloroplast of said protein of interest may result in a modulation of the chloroplast pathway, and altered production of a biomolecule derived from or produced in said chloroplast pathway. Accordingly, further disclosed herein is a method for modulating the production of a biomolecule of interest, said biomolecule being derived from, in particular produced in, a chloroplast pathway, said method comprising culturing a host cell comprising an exogenous nucleic acid comprising a nucleotide sequence encoding a chloroplast targeting peptide comprising the NgPRK BTS, operably linked to a nucleotide sequence encoding a modulator of an enzyme involved in said chloroplast pathway.

In further examples the protein of interest is not naturally present in the chloroplast. For example, the protein of interest may be an enzyme involved in a biochemical reaction or pathway which is not naturally present in the chloroplast. By nuclear expression and chloroplast targeting of said enzyme, the biochemical reaction or pathway can be ensured in the chloroplast, resulting either in improved properties of the host cell or production of a biomolecule resulting from said biochemical reaction or pathway. For example, the host cell, in particular the microalga, may be transformed with an exogenous nucleic acid comprising a nucleotide sequence encoding a chloroplast targeting peptide comprising the NgPRK BTS of SEQ ID NO: 8 or a variant thereof, operably linked to a nucleotide sequence encoding said enzyme, and culturing the recombinant host cell. Accordingly, also disclosed herein is a method for ensuring a biochemical reaction or pathway in the chloroplast. In particular embodiments, this is a method for the production of a biomolecule of interest, said method comprising culturing a host cell comprising an exogenous nucleic acid comprising a nucleotide sequence encoding a chloroplast targeting peptide comprising the NgPRK BTS of SEQ ID NO: 8 or a variant thereof, operably linked to a nucleotide sequence encoding an enzyme involved in said biochemical reaction or pathway.

In the methods for modulating or ensuring the production of a biomolecule of interest as taught herein, the enzymes or the modulators of the enzymes which ensure the production of said biomolecule of interest, may be native to the host cell, or heterologous proteins.

The methods for modulating the production of a biomolecule of interest as taught herein may further comprise the step of recovering the biomolecule of interest from the host cell or the culture medium. The recovery of the biomolecule of interest from het host cell may encompass harvesting the chloroplasts from the microalga and purifying the biomolecule of interest from the chloroplasts. Methods for harvesting chloroplast are described elsewhere herein. Suitable purification can be carried out by methods known to the person skilled in the art such as by using lysis methods, extraction, ion exchange resins, electrodialysis, nanofiltration, etc.

Related aspects are directed to uses of the recombinant host cells as taught herein for modulating chloroplast pathways or for modulating the production of a biomolecule derived from or produced in a chloroplast pathway.

The culture of the recombinant host cells in the methods described herein can be carried out by conventional methods of culture according to the particular host cell that has been selected for the transformation and the production of the protein of interest. In the herein described methods, the recombinant host cells are preferably cultured under "conditions suitable to ensure nuclear expression of the coding sequences", which means any condition that allows a host cell to (over)produce a protein of interest as described herein and to target the protein of interest to the chloroplast.

Suitable conditions include, for example, fermentation conditions. Fermentation conditions can comprise many parameters, such as temperature ranges, levels of aeration, and media composition. Each of these conditions, individually and in combination, allows the host cell to grow. To determine if conditions are sufficient to allow nuclear (over) expression, a host cell can be cultured, for example, for about 4, 8, 12, 18, 24, 36, or 48 hours. During and/or after culturing, samples can be obtained and analyzed to determine if the conditions allow nuclear (over)expression. For example, the host cells in the sample or the culture medium in which the host cells were grown can be tested for the presence of a desired product (e.g. a protein of interest or a biomolecule of interest). When testing for the presence of a desired product, assays, such as, but not limited to, sodium dodecyl sulfate polyacrylamide gel electrophoresis (SDS-PAGE), TLC, HPLC, GC/FID, GC/MS, LC/MS, MS, can be used.

Exemplary culture media include broths or gels. The host cells may be grown in a culture medium comprising a carbon source to be used for growth of the host cell. Exemplary carbon sources include carbohydrates, such as glucose, fructose, cellulose, or the like, that can be directly metabolized by the host cell. In addition, enzymes can be added to the culture medium to facilitate the mobilization (e.g., the depolymerization of starch or cellulose to fermentable sugars) and subsequent metabolism of the carbon source. A culture medium may optionally contain further nutrients as required by the particular strain, including inorganic nitrogen sources such as ammonia or ammonium salts, and the like, and minerals and the like. In particular embodiments, wherein phototrophic microalgae are used as host cells, the method may comprise providing recombinant microalgae as taught herein, and culturing said microalgae in photobioreactors or an open pond system using $CO_2$ and sunlight as feedstock.

Other growth conditions, such as temperature, cell density, and the like are generally selected to provide an economical process. Temperatures during each of the growth phase and the production phase may range from above the freezing temperature of the medium to about 50° C.

The culturing step of the methods of the invention may be conducted aerobically, anaerobically, or substantially anaerobically. Briefly, anaerobic conditions refer to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an N2/CO2 mixture or other suitable non-oxygen gas or gasses.

Advantageously, the present inventors found that the robust nuclear expression and accumulation of the protein of interest in the chloroplast is resistant to nitrogen starvation conditions. Hence, in certain embodiments of the herein described methods, the recombinant host cells may be cultured under conditions of nitrogen depletion (i.e. by growing the recombinant host cells in a culture medium that lacks a nitrogen source). These culturing conditions are particularly advantageous for proteins involved in chloroplast pathways that benefit from nitrogen starvation, such as proteins involved in TAG biosynthesis and storage, fatty acid biosynthesis, accumulation of chrysolaminarin or starch, lipid degradation and recycling, protein degradation, photosystem proteins, and transporter proteins.

The present invention will now be further illustrated by means of the following non-limiting examples.

EXAMPLES

Example 1: Identification of a Bipartite Targeting Sequence (BTS) Within the Phosphoribulokinase (PRK) of *Nannochloropsis gaditana*

The phosphoribulokinase (PRK) of *Nannochloropsis gaditana* was selected to identify a chloroplast targeting sequence. This enzyme catalyzes the conversion of ATP and D-ribulose-5-phosphate to ADP and D-ribulose-1,5-diphosphate in the Calvin cycle, and is located in the chloroplast stroma. In *N. gaditana*, PRK is encoded by a single exon gene (SEQ ID NO:1; identified as 'Naga_100157g10' in the *Nannochloropsis* Genome Portal, CRIBI Genomics, www.nannochloropsis.org).

The coding sequence of the NgPRK gene was translated in silico (SEQ ID NO:2), revealing the typical "AF" junction feature reported for heterokonts BTS (Gruber et al. 2007. Plant Mol Biol 64:519-30). The in silico protein sequence was further analyzed with SignalP, which predicts the occurrence of signal peptides. A strong cleavage prediction was found in correspondence of this "AF" signature (FIG. 2).

In heterokonts, properly functioning BTSs require the presence of a transit peptide-like region adjacent to the N-terminally located signal peptide of the plastid pre-proteins (Gruber et al. 2007). In order to identify the mature PRK protein, sequences from different plant and algae PRKs were retrieved from Uniprot (FIGS. 3 A-E) and a multi-sequence alignment was performed (FIG. 3F). The experimentally characterized transit peptides of these PRKs were removed from the multisequence alignment, allowing detection of the mature PRK protein sequence. The highly conserved amino acid sequence (light grey) was noted across organisms, which follows the highly variable addressing signal at the N-termini (CTP or BTS).

Cleavage of the mature *N. gaditana* PRK protein around the first 60 amino acids region was also supported by secondary structure predictions (CFSSP; http://www.biogem.org/tool/chou-fasman/) showing that a turn occurs exactly in that region (FIG. 4). This would likely expose the transit peptide-like region to the activity of a chloroplast protease, which leads to the mature PRK protein.

The identified NgPRK BTS sequence (SEQ ID NO:8) is:

MVKTAAVSLLALAGLASAFVPPTTNFRSANRWTIKAKDTSFTRNLMMKLG
AD and the identified nucleic acid sequence (SEQ ID NO:9) of the *N. gaditana* PRK BTS is therefore:

ATGGTCAAGACTGCCGCCGTAAGCCTCCTGGCCCTAGCCGGGCTCGCATC

TGCCTTCGTGCCCCCCACCACGAATTTTCGCAGCGCTAACAGATGGACGA

TTAAGGCCAAAGACACGTCCTTCACCCGCAACCTCATGATGAAGCTGGGC

GCGGAC

Example 2: NgPRK BTS Promotes Sustained and Uniform Transgene Expression

Material and Methods

Cell Cultivation

*Nannochloropsis gaditana* Lubian Strain CCMP526 (Culture Collection of Marine Phytoplankton, now known as NCMA: National Center for Marine Algae and Microbiota) was used in all experiments. *N. gaditana* was grown at 20° C. in 250 mL flask in artificial seawater (ESAW) medium (Table 1) using ten times enriched nitrogen and phosphate sources (5,49 $10^{-3}$ M $NaNO_3$ and 2,24 $10^{-4}$ $NaH_3PO_4$) called "10xESAW", or nitrogen-depleted medium, where $NaNO_3$ was omitted. Cells were grown on a 12:12 light (60 µE $m^{-2}$ $sec^{-1}$)/dark cycle. For nuclear transformation, cells were grown under constant light in f/2 medium (Table 1) until they reached the late exponential phase. All cultures were maintained on f/2 plates solidified with 1% agar under a 12:12 light/dark regime in presence (transformed strains) or absence (wild-type strain) of the selective antibiotic zeocin (7 µg $mL^{-1}$). When needed, cells were counted using a LUNA™ Automated Cell Counter following manufacturers instructions.

TABLE 1

Composition of the "10X ESAW" and "f/2" cultivation media.

| f/2 Medium Final Concentration (mM) | |
| --- | --- |
| Tris pH 8 | 40 |
| NaCl | 363 |
| $Na_2SO_4$ | 25 |
| KCl | 8.034875922 |
| $NaHCO_3$ | 2.071428571 |
| KBr | 0.725210084 |
| $H_3BO_3$ | 0.372168285 |
| NaF | 0.666825435 |
| $MgCl_2 \cdot 6H_2O$ | 47.17166749 |
| $CaCl_2 \cdot 2H_2O$ | 9.142235222 |
| $SrCl_2 \cdot 6H_2O$ | 0.081770443 |
| $NaNO_3$ | 0.88245676 |
| $NaH_2PO_4$ | 0.041673612 |
| $Na_2 EDTA \cdot 2H_2O$ | 0.011712873 |
| $FeCl_3 \cdot 6H_2O$ | 0.011653718 |
| $CuSO_4 \cdot 5H_2O$ | 4.00481E−05 |
| $Zn SO_4 \cdot 7H_2O$ | 7.65217E−05 |
| $CoCl_2 \cdot 6H_2O$ | 4.20345E−05 |
| $MnCl_2 \cdot 2H_2O$ | 0.001111797 |
| $Na_2MoO_4$ | 3.05974E−05 |
| biotin (vit. H) | 4.09316E−06 |
| Cobalamin (Vit. B12) | 7.37806E−07 |
| thiamine (vit. B1) | 0.000664872 |
| 10X ESAW Medium Final Concentration (mM) | |
| NaCl | 363 |
| $Na_2SO_4$ | 25 |
| KCl | 8.034875922 |
| $NaHCO_3$ | 2.071428571 |
| KBr | 0.725210084 |
| $H_3BO_3$ | 0.372168285 |
| NaF | 0.666825435 |
| $MgCl_2 \cdot 6H_2O$ | 47.17166749 |
| $CaCl_2 \cdot 2H_2O$ | 9.142235222 |
| $SrCl_2 \cdot 6H_2O$ | 0.081770443 |
| $NaNO_3$ | 5.49 |
| $NaH_2PO_4$ | 0.224 |
| $Na_2 EDTA \cdot 2H_2O$ | 0.0083 |
| Fe-EDTA | 0.00655 |
| $CuSO_4 \cdot 5H_2O$ | — |
| $Zn SO_4 \cdot 7H_2O$ | 0.000254 |
| $CoSO_4 \cdot 7H_2O$ | 0.0000569 |
| $MnSO_4 \cdot 7H_2O$ | 0.00242 |
| $Na_2MoO_4$ | — |
| biotin (vit. H) | 4.09316E−06 |
| Cobalamin (Vit. B12) | 7.37806E−07 |
| thiamine (vit. B1) | 0.000664872 |

Constructions eYFP (Protein GenBank: CCF77369.1) was selected as the reporter gene of choice to test the functionality of the identified BTS sequence in addressing nuclear-encoded protein to the chloroplast. To ensure correct expression and translation of the RNA into protein, the DNA sequence was codon-optimized for *Nannochloropsis* (http://www.kazusa.or.jp/codon/cgi-bin/showcodon.cgi?species=52230), resulting in the sequence below (SEQ ID NO:10). The initial ATG, when provided by the BTS sequence in the chimeric construct, was removed.

SEQ ID NO:10: eYFP encoding nucleotide sequence codon-optimized for expression in *Nannochloropsis*.

ATGGTCTCCAAGGGCGAGGAGCTCTTCACCGGCGTCGTCCCCATCCTCGT

CGAGCTCGACGGCGACGTCAACGGCCACAAGTTCTCCGTCTCCGGCGAGG

GCGAGGGCGACGCTACCTACGGCAAGCTCACCCTCAAGTTCATCTGCACC

ACCGGCAAGCTCCCCGTCCCCTGGCCCACCCTCGTCACCACCTTCGGCTA

CGGCCTCCAGTGCTTCGCTCGCTACCCCGACCACATGAAGCAGCACGACT

TCTTCAAGTCCGCTATGCCCGAGGGCTACGTCCAGGAGCGCACCATCTTC

TTCAAGGACGACGGCAACTACAAGACCCGCGCTGAGGTCAAGTTCGAGGG

CGACACCCTCGTCAACCGCATCGAGCTCAAGGGCATCGACTTCAAGGAGG

ACGGCAACATCCTCGGCCACAAGCTCGAGTACAACTACAACTCCCACAAC

GTCTACATCATGGCTGACAAGCAGAAGAACGGCATCAAGGTCAACTTCAA

GATCCGCCACAACATCGAGGACGGCTCCGTCCAGCTCGCTGACCACTACC

AGCAGAACACCCCCATCGGCGACGGCCCCGTCCTCCTCCCCGACAACCAC

TACCTCTCCTACCAGTCCGCTCTCTCCAAGGACCCCAACGAGAAGCGCGA

```
                     -continued
CCACATGGTCCTCCTCGAGTTCGTCACCGCTGCTGGCATCACCCTCGGCA

TGGACGAGCTCTACAAGTAA
```

Three different cassettes were synthesized by Thermo Scientific and subcloned via EcoRl/Ndel into the recipient *Nannochloropsis* overexpression plasmid pCT2Ng, thus generating:
pCT55 (PtAtpC_BTS::eYFP), where the *Phaeodactylum* BTS from the γ subunit of plastid ATP synthetase (AtpC) was fused to eYFP (Apt et al. 2002).
pCT56 (NgPRK_BTS::eYFP), where the NgPRK BTS identified in Example 1 was fused to eYFP
pCT59 (eYFP), lacking any BTS sequence and used as a positive control for cytosolic eYFP expression. This construct was obtained from amplification of the ΔAATG eYFP coding sequence with primers 'eYFP Fw2' (CCGCCGGAATTCATGGTCTCCAAGGGCGAGG, SEQ ID NO:11) and 'eYFP Rev2'(GAAAGTCCATATGT-TACTTGTAGAGCTCGTCCATG, SEQ ID NO:12), introducing the missing ATG and EcoRl/Ndel cloning sites.

All three pCT2Ng derivatives carry the shBle gene conferring resistance to the antibiotic Zeocin. In these plasmids, transcription is driven by the ubiquitin extension protein (UEP) promoter and terminated by the *Phaeodactylum* fucoxanthin chlorophyll binding protein (fcpA) terminator.

Figure 5F:
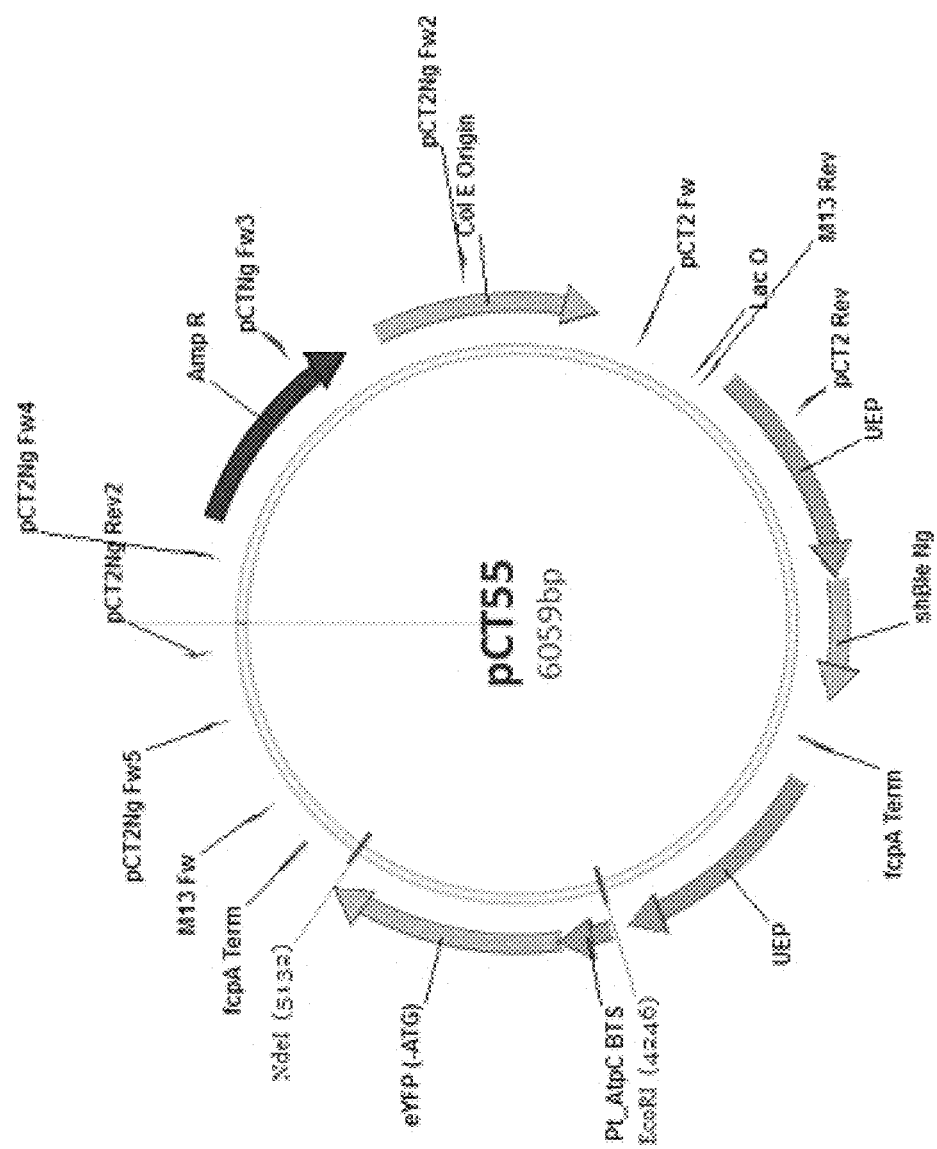
FIG. 5: DNA sequences (A-D, SEQ ID NO:13-16) of the recipient PCT2Ng vector (A,E) and the constructed cassettes for pCT55 (B,F), pCT56 (C,G) and pCT59 (D,H) and corresponding vector maps (E-H). EcoRI/NdeI restriction sites are highlighted in bold, whereas the used BTS sequences are underlined in the DNA sequences. UEP: ubiquitin extension protein promoter; fcpA Term: fucoxanthin chlorophyll binding protein terminator; MCS: multi cloning site. shBle Ng: *Nannochloropsis* codon-optimized selectable marker conferring resistance to Zeocin.
Figure 5G:
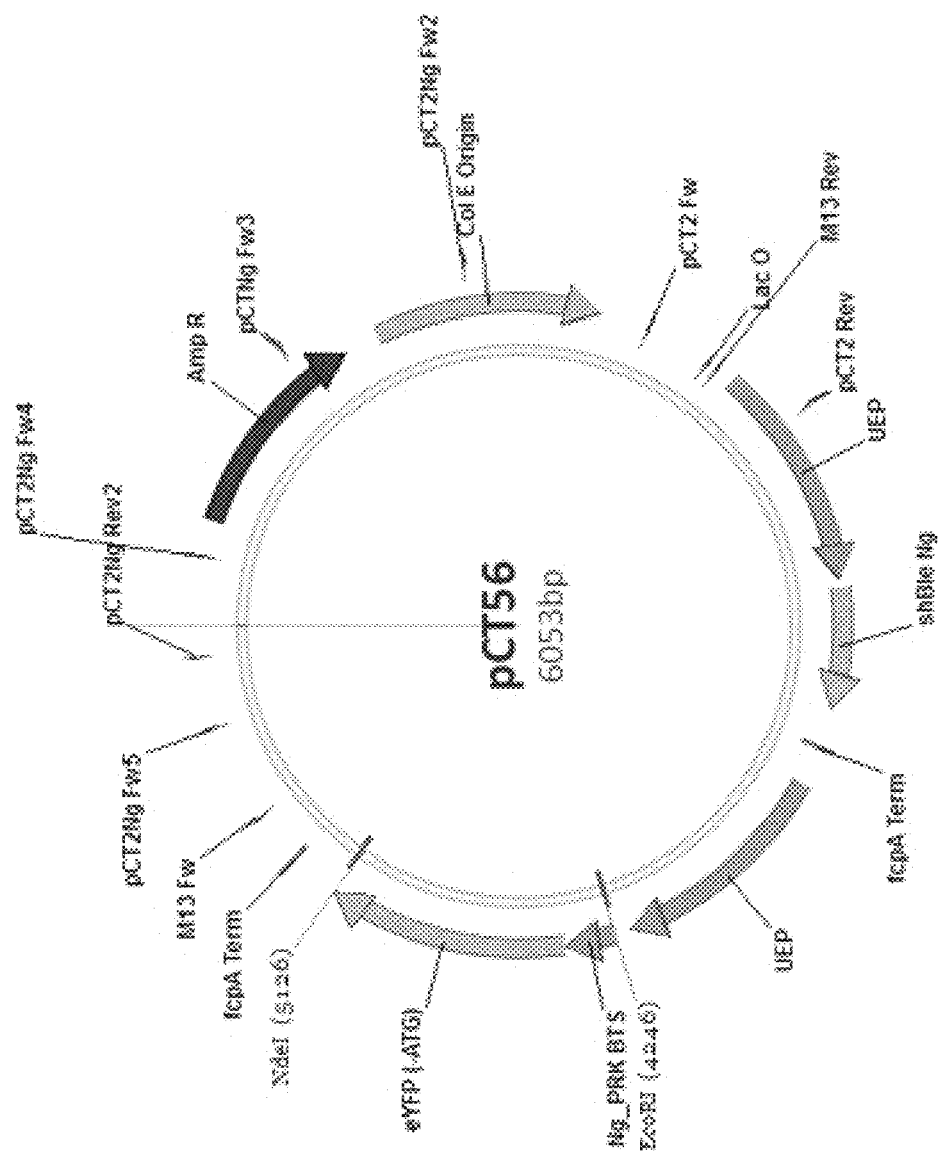
Figure 5H:
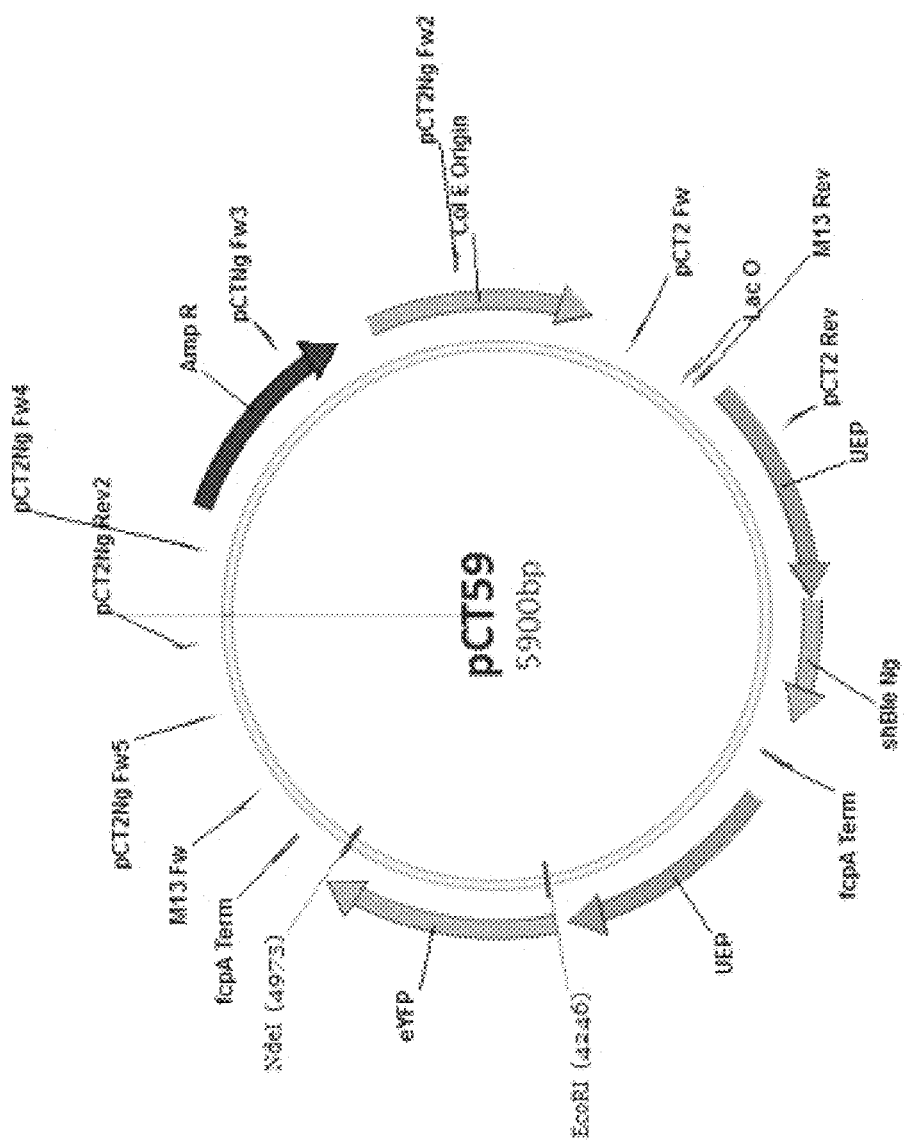

DNA sequences of the recipient pCT2Ng and of the three EcoRl/Ndel synthesized cassettes, and the corresponding vector maps are shown in FIG. 5.

Nuclear Transformation of *N. gaditana*

Plasmids pCT55, pCT56 and pCT59 were linearized by digestion with ScaI and column-purified by the NucleoSpin® Gel and PCR Clean-up kit (Macherey-Nagel) following manufacturer's instructions. One microgram linearized plasmid was electroporated into *Nannochloropsis gaditana* following the protocol published by Radakovits et al. (2012 Nat Commun doi: 10.1038/ncomms1688). Transformed lines were selected on f/2 plates containing 7 μg mL$^{-1}$ zeocin and correct integration of the cassettes was assessed by colony PCR with primers Cass02Ng Fw (CTTGGAATGTGGTCCTGGTT, SEQ ID NO:17) and eYFP Rev (GAACTTGAGGGTGAGCTTGC, SEQ ID NO:18), which bind to the UEP promoter and eYFP coding sequence, respectively.

Fluorescence Activated Cell Sorting (FACS)

A Becton Dickinson FACSCalibur and CellQuest Pro software (BD Biosciences, San Jose, Calif.) were used to measure the fluorescent intensity of single cells. Excitation was performed at 488 nm by an argon laser and a 530/30 fluorescence filter was used in FL1 to collect eYFP fuorescence.

Results

To validate NgPRK BTS functionality, transgenic *Nannochloropsis* lines overexpressing either the previously described *Phaeodactylum* AtpC BTS (pCT55) (Apt et al. 2002 J Cell Sci 115:4061-9) or the NgPRK BTS identified in Example 1 (pCT56) fused to a codon-optimised eYFP were generated. As an internal control, strains that accumulate eYFP in their cytosol (pCT59) were also included. We first checked whether the BTS sequences had an impact on the expression levels of the transgenes. Eleven pCT55 and eleven pCT56 clones were assessed for eYFP fluorescence on a single cell level by Fluorescence Assisted Cell Sorting (FACS), allowing a qualitatively and quantitatively estimate of protein expression across the cell line population. The untransformed wild-type strain (WT) was used as a negative control for eYFP accumulation in the analysis. Fluorescence collected in the YFP window for this strain was labelled as M1 (negative signal).

TABLE 2

FACS analysis on eleven randomly selected pCT55 clones. eYFP-expressing cells were gated in the M2 part of the graph (FIG. 6), whereas cells gated to the M1 were considered negative (see WT as a reference). By choosing an M2-gated cutoff at 10%, clones pCT55-2, 6, 7, 8 and 9 were selected as positives.

| | Marker | | | | | | | | |
|---|---|---|---|---|---|---|---|---|---|
| | All | | | M1 | | | M2 | | |
| Sample ID | % Gated | Mean | Median | % Gated | Mean | Median | % Gated | Mean | Median |
| WT | 100.00 | 4.43 | 3.79 | 95.85 | 4.05 | 3.79 | 2.53 | 21.02 | 19.46 |
| 55.1 | 100.00 | 5.31 | 4.37 | 93.37 | 4.51 | 4.26 | 5.52 | 19.91 | 15.96 |
| 55.2 | 100.00 | 7.54 | 6.32 | 82.25 | 5.76 | 5.57 | 17.72 | 16.01 | 13.22 |
| 55.3 | 100.00 | 3.83 | 3.08 | 92.98 | 3.42 | 3.08 | 3.28 | 18.60 | 14.59 |
| 55.4 | 100.00 | 5.64 | 4.78 | 94.61 | 4.92 | 4.66 | 5.10 | 19.48 | 15.19 |
| 55.5 | 100.00 | 5.52 | 3.52 | 89.13 | 3.68 | 3.40 | 8.72 | 25.46 | 21.29 |
| 55.6 | 100.00 | 14.10 | 5.52 | 80.61 | 5.07 | 4.83 | 19.29 | 51.96 | 29.96 |
| 55.7 | 100.00 | 12.29 | 5.00 | 77.88 | 4.60 | 4.29 | 21.78 | 40.00 | 26.18 |
| 55.8 | 100.00 | 8.35 | 5.00 | 85.60 | 4.83 | 4.61 | 14.05 | 30.00 | 23.71 |
| 55.9 | 100.00 | 25.83 | 21.29 | 41.75 | 4.62 | 4.37 | 58.04 | 41.18 | 35.55 |
| 55.10 | 100.00 | 4.67 | 3.68 | 94.12 | 3.91 | 3.62 | 4.55 | 21.58 | 19.11 |
| 55.11 | 100.00 | 5.45 | 3.19 | 89.12 | 3.43 | 3.11 | 7.61 | 31.11 | 22.88 |

TABLE 3

FACS analysis on eleven randomly selected pCT56 clones.
eYFP-expressing cells were gated in the M2 part of the graph
(FIG. 7), whereas cells gated to the M1 were considered negative
(see WT as a reference). By choosing an M2-gated cutoff at 10%,
clones pCT56-2, 3, 4, 6, 7, 10 and 11 were considered positives.

| | Marker | | | | | | | | |
|---|---|---|---|---|---|---|---|---|---|
| | All | | | M1 | | | M2 | | |
| Sample iD | % Gated | Mean | Median | % Gated | Mean | Median | % Gated | Mean | Median |
| WT | 100.00 | 4.61 | 3.96 | 96.26 | 4.18 | 3.92 | 2.66 | 21.70 | 20.17 |
| 56.1 | 100.00 | 3.81 | 3.05 | 93.40 | 3.38 | 3.05 | 3.00 | 20.52 | 15.61 |
| 56.2 | 100.00 | 19.78 | 17.78 | 9.88 | 8.75 | 9.14 | 90.47 | 20.96 | 18.77 |
| 56.3 | 100.00 | 12.67 | 5.47 | 71.55 | 4.76 | 4.41 | 28.19 | 32.90 | 24.36 |
| 56.4 | 100.00 | 18.51 | 17.31 | 8.73 | 9.03 | 9.39 | 91.71 | 19.38 | 17.94 |
| 56.5 | 100.00 | 5.83 | 4.29 | 93.11 | 4.43 | 4.18 | 6.34 | 26.96 | 24.36 |
| 56.6 | 100.00 | 10.86 | 5.47 | 83.31 | 5.15 | 4.96 | 16.64 | 39.53 | 27.38 |
| 56.7 | 100.00 | 17.75 | 15.96 | 12.21 | 8.96 | 9.31 | 88.27 | 18.93 | 17.00 |
| 56.8 | 100.00 | 5.07 | 4.53 | 97.42 | 4.68 | 4.49 | 2.29 | 22.03 | 20.35 |
| 56.9 | 100.00 | 6.84 | 4.49 | 90.28 | 4.53 | 4.26 | 9.31 | 29.58 | 22.77 |
| 56.10 | 100.00 | 43.86 | 40.68 | 4.94 | 5.77 | 5.62 | 95.05 | 45.85 | 41.79 |
| 56.11 | 100.00 | 7.40 | 5.19 | 89.10 | 5.08 | 4.87 | 10.72 | 26.84 | 21.87 |

Figure 6C:
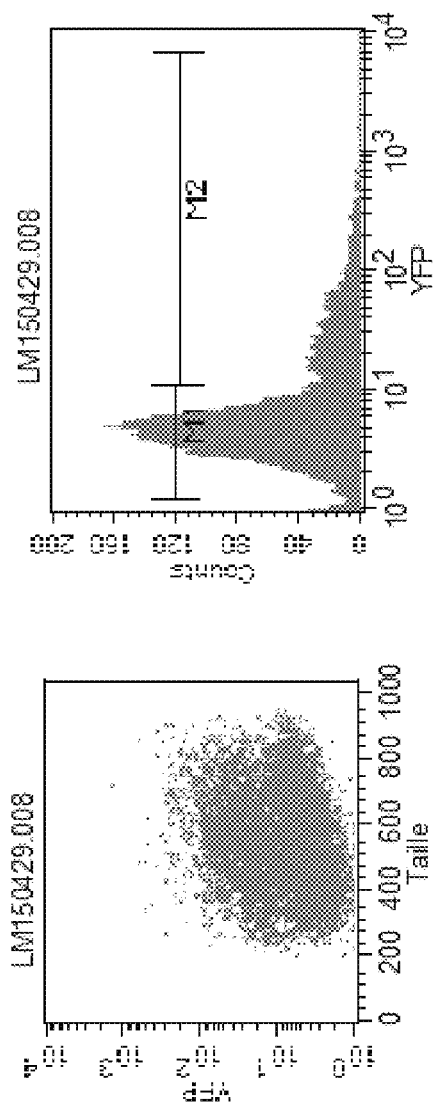
FIG. 6: Representative FACS analysis of wild-type *N. gaditana* (A, Sample ID: WT), and negative (B, Sample ID: 55.3) and positive (C, Sample ID:55.7) pCT55 clones. eYFP-expressing cells were gated in the M2 part of the graph, whereas cells gated to the M1 were considered negative (see WT as a reference). M2-gated cutoff was chosen at 10% for identifying positive clones.

The results obtained for pCT55 (PtAtpC BTS::eYFP; FIG. 6, Table 2) and pCT56 (NgPRK BTS::eYFP; FIG. 7, Table 3) show that 45% of the pCT55 and 63% of the pCT56 clones expressed eYFP to a level higher than the defined cut-off of 10% in the M2.

Although the observed different percentage of the eYFP-positive clones between pCT55 and pCT56 could have arisen from random transgene integration and position effects, a closer look at the FACS analysis indicates that transgene (eYFP) expression across cell populations is on average very uniform in pCT56 positive lines when compared to their pCT55 counterparts, as highlighted by the higher percentage of M2-gated cells.

A similar yet not as uniform expression pattern was observed for six pCT59 positive clones which express eYFP in the cytosol (FIG. 8, Table 4).

In conclusion, the NgPRK BTS promotes sustained and uniform transgene expression.

Example 3: Targeting of Nuclear-Encoded Recombinant Proteins Into the Chloroplast Via Fusion to the BTS of NgPRK Materials and Methods See Example 2 for the generation of the constructs, nuclear transformation of *N. gaditana* and cell culture.

Confocal Microscopy

Functionality of the different BTS was assessed by imaging the subcellular chlorophyll and YFP fluorescence by confocal laser scanning microscopy with a Leica TCS-SP2 operating system (Leica, Heidelberg, Germany). Chlorophyll was excited at 633 nm and the emitted fluorescence was detected between 650 and 750 nm. YFP was excited at 488 nm and emitted fluorescence was detected between 510 and 545 nm.

TABLE 4

FACS analysis six positive pCT59 clones that express eYFP
in the cytosol. eYFP-expressing cells were gated in the M2
part of the graph (FIG. 8), whereas cells gated to the M1
were considered negative (see WT as a reference).
M2-gated cutoff was chosen at 10%.

| | Marker | | | | | | | | |
|---|---|---|---|---|---|---|---|---|---|
| | All | | | M1 | | | M2 | | |
| Sample ID | % Gated | Mean | Median | % Gated | Mean | Median | % Gated | Mean | Median |
| WT | 100.00 | 4.37 | 4.00 | 95.18 | 4.35 | 4.03 | 1.56 | 13.21 | 11.97 |
| 59-10 | 100.00 | 51.26 | 40.68 | 8.16 | 7.13 | 7.43 | 91.89 | 55.16 | 43.71 |
| 59-11 | 100.00 | 18.27 | 8.28 | 62.32 | 6.09 | 6.04 | 37.81 | 38.41 | 24.36 |
| 59-12 | 100.00 | 8.70 | 7.77 | 75.91 | 6.70 | 6.73 | 24.60 | 14.95 | 12.98 |
| 59-13 | 100.00 | 9.91 | 6.98 | 79.53 | 6.17 | 6.15 | 20.65 | 24.44 | 15.26 |
| 59-14 | 100.00 | 27.28 | 17.47 | 25.78 | 7.36 | 7.64 | 74.57 | 34.10 | 23.71 |
| 59-15 | 100.00 | 32.59 | 18.11 | 19.83 | 7.93 | 8.28 | 80.55 | 38.55 | 21.67 |

Western Blotting

*Nannochloropsis* total protein extracts were obtained from frozen cell pellets resulting from 50 mL of cell cultures in the exponential phase. Whole proteins were extracted with a micotube pestel after addition of 200 μL of extraction buffer (30 mM pyrophosphate tetrasodium, 100 mM Tris-HCl pH 6.8, 1% SDS). The cell extract was centrifuged for 5 minutes at 13200 rpm and the supernatant quantified using the Bio-Rad protein assay reagent (Bio-Rad, Hercules, Calif.). Proteins (15 to 40 μg) were loaded on 12% acrylamide gels (TGX Stain-Free™, FastCast™, BioRad Cat. 161-0185) for SDS-PAGE analyses. For Western blot analyses, proteins were transferred to a nitrocellulose membrane (BA85, Schleicher & Schuell). eYFP fusions were detected using a commercially available αGFP mouse monoclonal antibody (GFP-2A5, Euromedex, 67458 Mundolsheim, France) at a 1/3300 dilution. Processing of Western Blots images was performed with the Image Lab 5.1 Software (Bio-Rad, Hercules, Calif.).

Results

Based on the FACS results, one clone showing the highest eYFP expression for each strain was selected and subcellular localization of the fluorescent marker was assessed by means of confocal microscopy. pCT55-9 was selected for the PtAtpC BTS::eYFP strain, pCT56-10 was selected for the NgPRK BTS::eYFP strain, and pCT59-10 was selected for the strain with cytosolic eYFP expression.

Figure 9:
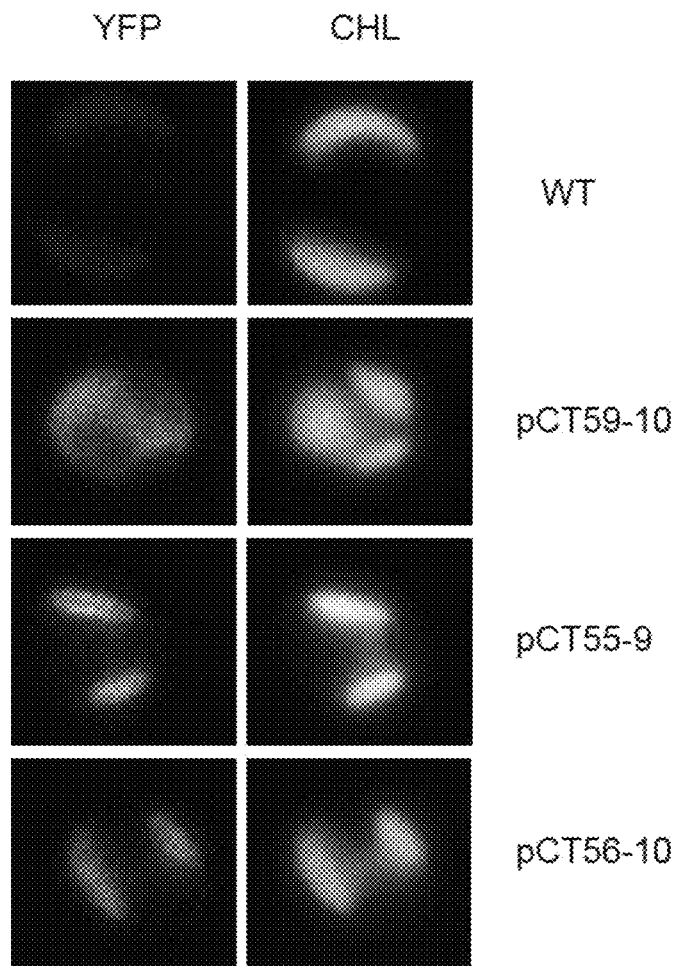
FIG. 9: Representative confocal microscopy images of positive pCT59, pCT55 and pCT56 clones showing highest eYFP expression. YFP: eYFP signal; CHL: chlorophyll fluorescence. A wild-type (WT) strain was used to set the background for eYFP detection, whereas an eYFP control was used as a marker for cytosolic localization.

As shown in FIG. 9, eYFP fusions with either the BTS from *Phaeodactylum* AtpC (pCT55-9) or the BTS from *Nannochloropsis* PRK (pCT56-10) resulted in a perfect overlay between eYFP and chlorophyll fluorescence, indicative of chloroplast localization. The strain where the eYFP sequence was not preceded by any BTS (pCT59-10) showed, as expected, a complete separation between eYFP and chlorophyll fluorescence, indicative of cytosolic eYFP expression.

Figure 10A:
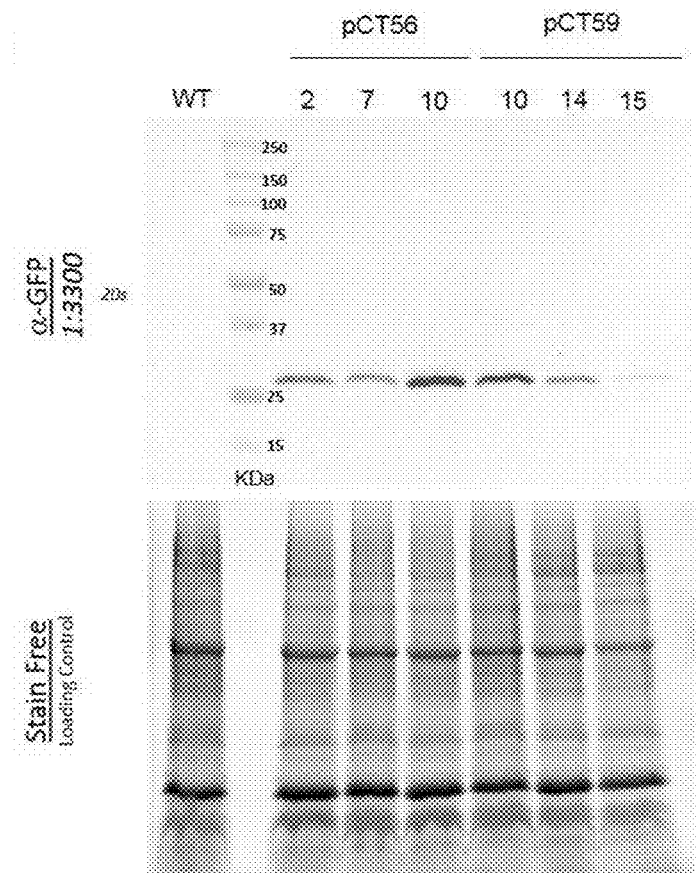
FIG. 10: Assessment of eYFP expression levels in pCT56 and pCT59 strains. (A) Western Blot analysis on three pCT56 and pCT59 clones (top) and stain free control of gel loading (bottom). (B) Quantification of western blots bands intensity by the Image Lab 5.1 software (Biorad); values are relative to the highest intensity band of pCT56-10, which was set to 100. AVG: averaged band intensity of pCT56 and pCT59 clones.
Figure 10B:
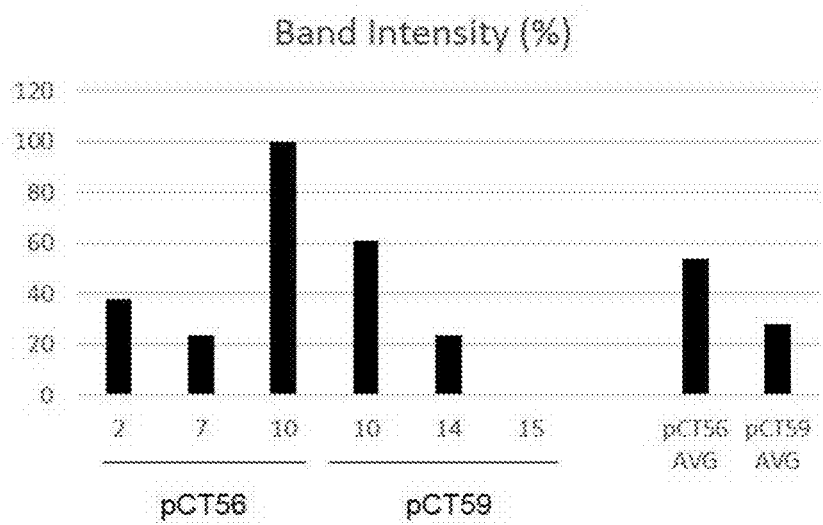

Correct processing of the NgPRK BTS and higher expression of the eYFP marker in pCT56 strains when compared to their cytosolic pCT59 counterparts was also assessed by Western blots as an independent confirmation of FACS analyses on three independently generated clones per strain (FIG. 10).

Example 4: NgPRK BTS Promotes Sustained Transgene Expression Under Nitrogen Starvation Conditions

Materials and Methods

See Example 2 for the generation of the constructs, nuclear transformation of *N. gaditana* and cell culture, and Example 3 for Western blotting.

Results

Figure 11A:
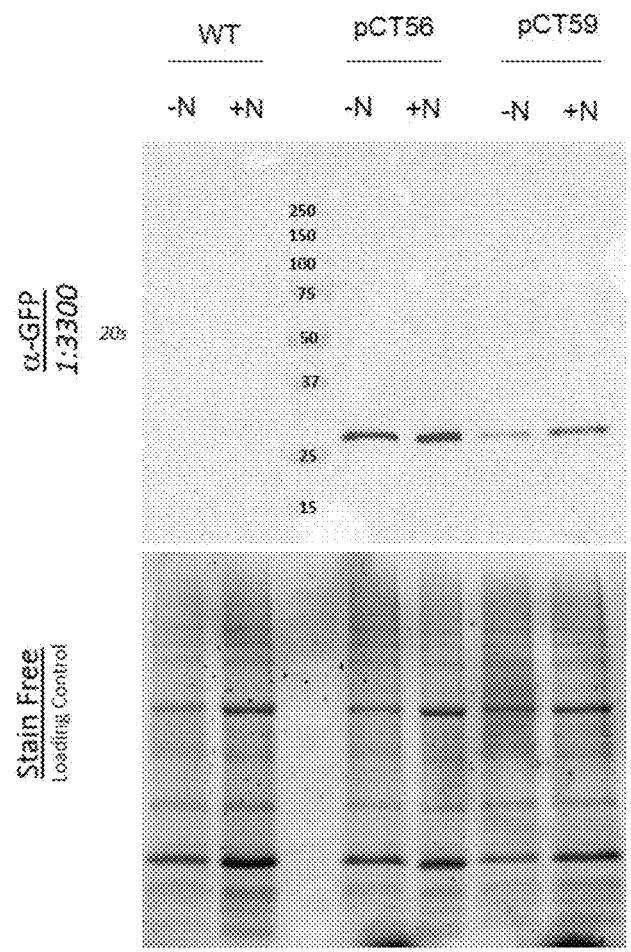
FIG. 11: Assessment of eYFP expression levels in pCT56-10 and pCT59-10 strains under nitrogen deplete (−N) and nitrogen replete (+N) media conditions. (A) Western Blot analysis on pCT56-10 and pCT59-10 clones (top) and stain free control of gel loading (bottom). WT was used as a negative control. (B) Quantification of western blots bands reported in (A) by the Image Lab 5.1 software (Bio-Rad). Reduction in band intensity was calculated as a percentage of the "−N" band intensity relative to the "+N" band within the same clone.
Figure 11B:
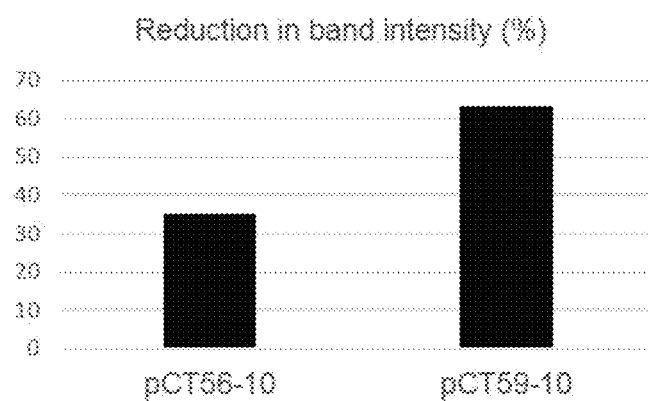

In order to evaluate the efficiency of the identified NgPRK BTS identified in Example 1 in promoting robust accumulation of recombinant proteins in the *Nannochloropsis* chloroplast under conditions of nitrogen starvation, eYFP accumulation was checked in the pCT56-10 and pCT59-10 clones under both nitrogen replete and deplete conditions (FIG. 11). Nitrogen and phosphorous starvation is known to trigger triacylglycerol (TAG) accumulation in algae (Abida et al. 2015. Plant Physiology.167(1): 118-136), but results in global down-regulation of protein expression, with some specific exceptions (Dong et al. 2013 Plant Physiol. 162(2): 1110-1126). The results show that the NgPRK_BTS::eYFP chimeric protein had almost half of the reduction in protein expression when compared to the clone expressing cytosolic eYFP (pCT59-10).

The invention claimed is:

1. An isolated nucleic acid comprising:
   (a) a first nucleotide sequence having at least 98% sequence identity to SEQ ID NO: 9, wherein said first nucleotide sequence encodes a chloroplast targeting peptide; and, operably linked to the first nucleotide sequence,
   (b) a second nucleotide sequence encoding a protein of interest, wherein the protein of interest is not *Nannochloropsis gaditana* phoshoribulokinase (PRK).

2. A nucleic acid expression cassette comprising (a) a first nucleotide sequence encoding a chloroplast targeting peptide operably linked to a second nucleotide sequence encoding a protein of interest that is not *Nannochloropsis gaditana* PRK and (b) a promoter and a terminator operably linked to the first and second nucleotide sequences,
   wherein the chloroplast targeting peptide comprises SEQ ID NO: 8, and
   wherein the expression cassette ensures expression of the first and second nucleotide sequences in the nucleus of a host cell transformed with said expression cassette.

3. The expression cassette according to claim 2, wherein the protein of interest is an enzyme or a modulator of an enzyme involved in a chloroplast biochemical reaction or pathway.

4. The expression cassette according to claim 2, wherein the protein of interest is an enzyme or a modulator of an enzyme involved in lipid biosynthesis such as TAG biosynthesis and storage, and fatty acid biosynthesis, or involved in chrysolaminarin or starch accumulation.

5. The expression cassette according to claim 2, wherein the protein of interest is selected from the group consisting of a chloroplast transporter, a protein of transcription or translation machinery, a transcription factors/enhancer/silencer, a nuclease, and a chaperone.

6. A vector comprising the expression cassette according to claim 2.

7. A recombinant host cell which has been transformed with the expression cassette according to claim 2 or the vector according to claim 6, wherein said host cell is a microalga.

8. The host cell according to claim 7, wherein said microalga is a *Nannochloropsis* species or a *Phaeodactylum* species.

9. The host cell according to claim 7, wherein said microalga is the diatom *Nannochloropsis gaditana*.

10. A method for producing a protein of interest in the chloroplast of a microalga, said method comprising:
    culturing a recombinant microalga that has been transformed with a nucleic acid comprising a nucleotide sequence encoding a chloroplast targeting peptide operably linked to a nucleotide sequence encoding the protein of interest, wherein the protein of interest is not *Nannochloropsis gaditana* phoshoribulokinase (PRK), and
    wherein the chloroplast targeting peptide comprises SEQ ID NO: 8.

11. The method according to claim 10 further comprising the steps of:
    harvesting the chloroplast from the microalga; and
    purifying the protein of interest from the chloroplast.

12. The method according to claim 10, wherein the recombinant microalga is cultured under conditions of nitrogen depletion.

13. The isolated nucleic acid of claim 1, wherein the first nucleotide sequence encodes a polypeptide comprising SEQ ID NO:8.

14. The isolated nucleic acid of claim 1, wherein the first nucleotide sequence is SEQ ID NO:9.

* * * * *

SEQUENCE LISTING

```
<160> NUMBER OF SEQ ID NOS: 19

<210> SEQ ID NO 1
<211> LENGTH: 2638
<212> TYPE: DNA
<213> ORGANISM: Nannochloropsis gaditana

<400> SEQUENCE: 1
gttgcgtaac acttcttctg atgaggtgca ttggatggtg tcgtacgtgt tttcgcctcc      60
tcgtccacac catccgactg tttgtaccca tgatgacgcg atcacaccgt cttcacgggt     120
tgggacactg tcgtcttgct gtttgtcaac gtgccacgct acctcgcctt cgacaaagat     180
ctccatgcca tccgcggccg ggaatacctg gattttggca tagctcccac atcatgggga     240
aattcggcat gccacaccgc tcatttaact cctgagcgct gcaacatgtg caagccaagc     300
gccaagacgc ccgagccact tgttcagttc tcaagagggg ccgggaggat cgtcgcgggc     360
ttcgatgaaa gcgtctccgc ttcagtttaa gcccagcgt cattcatagt cacgttgttt      420
ttctcacaaa atctcatttt tccttgcaga agtatggtca agactgccgc cgtaagcctc     480
ctggccctag ccgggctcgc atctgccttc gtgccccca ccacgaattt tcgcagcgct     540
aacagatgga cgattaaggc caaagacacg tccttcaccc gcaacctcat gatgaagctg     600
ggcgcggacg acaaggtcat tttgatcggc gtggccgcgg attccggctg tggaaagtcg     660
acgttcatgc ggcggctgac caacatcttt ggtgggagca acgtgggccc cctggggggc     720
```

```
ggtttcgaca acgggggatg ggagacgaac accctggtct cggacacgac caccgtcatc    780
tgcttggacg actaccatgc caacgaccgc tctgggcgga aagtgacggg ccgcaccgcc    840
ttggaagctg ccgagcagaa ttttgacctc atgtacgagc agctcaaggc cctgaaggag    900
ggcaaaactg tggccaagcc catctacaac acgtgaacg ggaccttgga ccggcccgag    960
gaggtggtgc ccacccccat tgtgatcgtg gagggcttgc accctggta cgacgcccgc   1020
gtcaaggacc tgctcgacta cactatctac ctggacatat cggacgagat caagcgcgca   1080
tggaagatcc agcgggacat ggccgagcgc ggatggacct ggagcaggt ggaggcagag   1140
attgaaaagc gtaagccgga cttcaataaa ttcgtgggc cccagaagga ggtagccgac   1200
tcggtgatcc aagtcttgcc cacagagctg accaacgacc ccgaggggaa gatcctccgc   1260
gtccggctca tccagaagga gacggggac tacgaacccg tctacctgtt cgaccagggc   1320
tctacggtct cctggattcc ctgcggcacg aagctgacat gctcctaccc cggcatcaag   1380
ctgggctcgg gaccggaccg ctggttcaac aacgcggtga acgtggtgga gatgacggc    1440
cagtttgaca agctggaaga gcttgcctac gtggagaagc acctggggaa cacggccagc   1500
aagtacgacg gggagatcac ggcccagatg ctcaagaacg agggcccccg ggaccctgaa   1560
cggctcaggc ctcttccaga ccatcgtctc gctcaagatc cgcgaggtct acgagaagct   1620
gagcgggaag aaggtagacg cctccgtcaa ggccccgtg gccgcgtaag ccggcggcaa    1680
aggagcgagg gctggttggc tgctgaaaac agggtaggct ttgaggtgtg gagatcgtaa   1740
cggctcccac cggaccctcag cagcatccct tgaacaaacg gcgagcctca cacgccgact  1800
gctgcatgtt ttgtgtgttc tgtgcttttc gtgtccggag ccatcgcgtc gtctgcgccg   1860
ggtgccgggc ccagagagcg gggggagggc cagggaggca ttctgttgtt ttgggtggtg   1920
tttgggggat aggagactga cctgtcggcc ccttttttgac gtatcgcgaa tttcgatgaa   1980
ataatcggct ccattctcca ttaaattgaa gcatgcatgg atgatgatcg aggtgggagg   2040
ggcgcctata acaccgccac ctgtgtccct gggcgagctc ttcgggttcc tttacttttc    2100
gactccgaaa acgcttttct gaaacaaagt cgccaaggtt actcgctgtt gcccataccc   2160
cttccattcg cgagtctaga actccttgca gatccctgga taagagattc aaaaacgttg   2220
cggccgagga gtcgatggaa tgcctccctc cttgaacccg ccggcctgc gcgtgctcat    2280
ggctcgtgac agacacccat gtcgacctcg cctgcgggga gaaacagag cgtccgaaaa    2340
cagcgcaaag ggagtccgag aactgcgcaa agaaagtccg agagcagcgc gcagcaaaag   2400
cgagggtcct tgtggcctga tttcatcgtg gaagatgtta cgaatcacga cttatgcgca   2460
ccacttcact tcatcgaagc gcgatcctgt ttatactttc tactgcacaa aattgtgtgt   2520
cgatcccctc cttctccccc tctcctcctc tccctcgcct cactcatcta aatggcgtgc   2580
cagcacatga taggtggcgt catagcaggg taaaattaca ctggccacgg gcacggcc    2638
```

<210> SEQ ID NO 2
<211> LENGTH: 428
<212> TYPE: PRT
<213> ORGANISM: Artificial Sequence
<220> FEATURE:
<223> OTHER INFORMATION: In silico protein sequence of Nannochloropsis
gaditana phosphoribulokinase

<400> SEQUENCE: 2

Met Val Lys Thr Ala Ala Val Ser Leu Leu Ala Leu Ala Gly Leu Ala
1               5                   10                  15

```
Ser Ala Phe Val Pro Thr Thr Asn Phe Arg Ser Ala Asn Arg Trp
             20                  25                  30

Thr Ile Lys Ala Lys Asp Thr Ser Phe Thr Arg Asn Leu Met Met Lys
         35                  40                  45

Leu Gly Ala Asp Asp Lys Val Ile Leu Ile Gly Val Ala Ala Asp Ser
     50                  55                  60

Gly Cys Gly Lys Ser Thr Phe Met Arg Arg Leu Thr Asn Ile Phe Gly
 65                  70                  75                  80

Gly Ser Asn Val Gly Pro Leu Gly Gly Phe Asp Asn Gly Gly Trp
                 85                  90                  95

Glu Thr Asn Thr Leu Val Ser Asp Thr Thr Val Ile Cys Leu Asp
                100                 105                 110

Asp Tyr His Ala Asn Asp Arg Ser Gly Arg Lys Val Thr Gly Arg Thr
             115                 120                 125

Ala Leu Glu Ala Ala Glu Gln Asn Phe Asp Leu Met Tyr Glu Gln Leu
         130                 135                 140

Lys Ala Leu Lys Glu Gly Lys Thr Val Ala Lys Pro Ile Tyr Asn His
145                 150                 155                 160

Val Asn Gly Thr Leu Asp Arg Pro Glu Glu Val Val Pro Thr Pro Ile
                165                 170                 175

Val Ile Val Glu Gly Leu His Pro Trp Tyr Asp Ala Arg Val Lys Asp
            180                 185                 190

Leu Leu Asp Tyr Thr Ile Tyr Leu Asp Ile Ser Asp Glu Ile Lys Arg
         195                 200                 205

Ala Trp Lys Ile Gln Arg Asp Met Ala Glu Arg Gly Trp Thr Leu Glu
     210                 215                 220

Gln Val Glu Ala Glu Ile Glu Lys Arg Lys Pro Asp Phe Asn Lys Phe
225                 230                 235                 240

Val Gly Pro Gln Lys Glu Val Ala Asp Ser Val Ile Gln Val Leu Pro
                245                 250                 255

Thr Glu Leu Thr Asn Asp Pro Glu Gly Lys Ile Leu Arg Val Arg Leu
            260                 265                 270

Ile Gln Lys Glu Thr Gly Asp Tyr Glu Pro Val Tyr Leu Phe Asp Gln
         275                 280                 285

Gly Ser Thr Val Ser Trp Ile Pro Cys Gly Thr Lys Leu Thr Cys Ser
     290                 295                 300

Tyr Pro Gly Ile Lys Leu Gly Ser Gly Pro Asp Arg Trp Phe Asn Asn
305                 310                 315                 320

Ala Val Asn Val Val Glu Met Asp Gly Gln Phe Asp Lys Leu Glu Glu
                325                 330                 335

Leu Ala Tyr Val Glu Lys His Leu Gly Asn Thr Ala Ser Lys Tyr Asp
            340                 345                 350

Gly Glu Ile Thr Ala Gln Met Leu Lys Asn Glu Gly Pro Arg Asp Pro
         355                 360                 365

Glu Arg Leu Arg Pro Leu Pro Asp His Arg Leu Ala Gln Asp Pro Arg
     370                 375                 380

Gly Leu Arg Glu Ala Glu Arg Glu Gly Arg Arg Leu Arg Gln Gly
385                 390                 395                 400

Pro Arg Gly Arg Val Ser Arg Arg Gln Arg Ser Glu Gly Trp Leu Ala
                405                 410                 415

Ala Glu Asn Arg Val Gly Phe Glu Val Trp Arg Ser
            420                 425
```

-continued

```
<210> SEQ ID NO 3
<211> LENGTH: 395
<212> TYPE: PRT
<213> ORGANISM: Arabidopsis thaliana

<400> SEQUENCE: 3

Met Ala Val Ser Thr Ile Tyr Ser Thr Gln Ala Leu Asn Ser Thr His
1               5                   10                  15

Phe Leu Thr Ser Ser Ser Ser Lys Gln Val Phe Leu Tyr Arg Arg
            20                  25                  30

Gln Pro Gln Thr Asn Arg Arg Phe Asn Thr Leu Ile Thr Cys Ala Gln
            35                  40                  45

Glu Thr Ile Val Ile Gly Leu Ala Ala Asp Ser Gly Cys Gly Lys Ser
    50                  55                  60

Thr Phe Met Arg Arg Leu Thr Ser Val Phe Gly Gly Ala Ala Lys Pro
65              70                  75                  80

Pro Lys Gly Gly Asn Pro Asp Ser Asn Thr Leu Ile Ser Asp Thr Thr
                85                  90                  95

Thr Val Ile Cys Leu Asp Asp Tyr His Ser Leu Asp Arg Tyr Gly Arg
            100                 105                 110

Lys Glu Gln Lys Val Thr Ala Leu Asp Pro Arg Ala Asn Asp Phe Asp
        115                 120                 125

Leu Met Tyr Glu Gln Val Lys Ala Leu Lys Asn Gly Ile Ala Val Glu
    130                 135                 140

Lys Pro Ile Tyr Asn His Val Thr Gly Leu Leu Asp Pro Pro Glu Leu
145                 150                 155                 160

Ile Gln Pro Pro Lys Ile Leu Val Ile Glu Gly Leu His Pro Met Phe
                165                 170                 175

Asp Glu Arg Val Arg Asp Leu Leu Asp Phe Ser Ile Tyr Leu Asp Ile
            180                 185                 190

Ser Asn Glu Val Lys Phe Ala Trp Lys Ile Gln Arg Asp Met Ala Glu
        195                 200                 205

Arg Gly His Ser Leu Glu Ser Ile Lys Ala Ser Ile Glu Ala Arg Lys
    210                 215                 220

Pro Asp Phe Asp Ala Phe Ile Asp Pro Gln Lys Gln Tyr Ala Asp Ala
225                 230                 235                 240

Val Ile Glu Val Leu Pro Thr Thr Leu Ile Pro Asp Asp Asn Glu Gly
                245                 250                 255

Lys Val Leu Arg Val Arg Leu Ile Met Lys Glu Gly Val Lys Tyr Phe
            260                 265                 270

Ser Pro Val Tyr Leu Phe Asp Glu Gly Ser Thr Ile Ser Trp Ile Pro
        275                 280                 285

Cys Gly Arg Lys Leu Thr Cys Ser Tyr Pro Gly Ile Lys Phe Asn Tyr
    290                 295                 300

Glu Pro Asp Ser Tyr Phe Asp His Glu Val Ser Val Leu Glu Met Asp
305                 310                 315                 320

Gly Gln Phe Asp Arg Leu Asp Glu Leu Ile Tyr Val Glu Ser His Leu
                325                 330                 335

Ser Asn Leu Ser Thr Lys Phe Tyr Gly Glu Val Thr Gln Gln Met Leu
            340                 345                 350

Lys His Ala Asp Phe Pro Gly Ser Asn Asn Gly Thr Gly Leu Phe Gln
        355                 360                 365

Thr Ile Val Gly Leu Lys Ile Arg Asp Leu Tyr Glu Gln Leu Ile Ala
    370                 375                 380
```

Asn Lys Ala Thr Ala Arg Ala Glu Ala Lys Ala
385                 390                 395

<210> SEQ ID NO 4
<211> LENGTH: 402
<212> TYPE: PRT
<213> ORGANISM: Spinacia oleracea

<400> SEQUENCE: 4

Met Ala Val Cys Thr Val Tyr Thr Ile Pro Thr Thr Thr His Leu Gly
1               5                   10                  15

Ser Ser Phe Asn Gln Asn Asn Lys Gln Val Phe Phe Asn Tyr Lys Arg
            20                  25                  30

Ser Ser Ser Ser Asn Asn Thr Leu Phe Thr Thr Arg Pro Ser Tyr Val
        35                  40                  45

Ile Thr Cys Ser Gln Gln Gln Thr Ile Val Ile Gly Leu Ala Ala Asp
    50                  55                  60

Ser Gly Cys Gly Lys Ser Thr Phe Met Arg Arg Leu Thr Ser Val Phe
65                  70                  75                  80

Gly Gly Ala Ala Glu Pro Pro Lys Gly Gly Asn Pro Asp Ser Asn Thr
                85                  90                  95

Leu Ile Ser Asp Thr Thr Val Ile Cys Leu Asp Asp Phe His Ser
                100                 105                 110

Leu Asp Arg Asn Gly Arg Lys Val Glu Lys Val Thr Ala Leu Asp Pro
            115                 120                 125

Lys Ala Asn Asp Phe Asp Leu Met Tyr Glu Gln Val Lys Ala Leu Lys
    130                 135                 140

Glu Gly Lys Ala Val Asp Lys Pro Ile Tyr Asn His Val Ser Gly Leu
145                 150                 155                 160

Leu Asp Pro Pro Glu Leu Ile Gln Pro Pro Lys Ile Leu Val Ile Glu
                165                 170                 175

Gly Leu His Pro Met Tyr Asp Ala Arg Val Arg Glu Leu Leu Asp Phe
            180                 185                 190

Ser Ile Tyr Leu Asp Ile Ser Asn Glu Val Lys Phe Ala Trp Lys Ile
    195                 200                 205

Gln Arg Asp Met Lys Glu Arg Gly His Ser Leu Glu Ser Ile Lys Ala
210                 215                 220

Ser Ile Glu Ser Arg Lys Pro Asp Phe Asp Ala Tyr Ile Asp Pro Gln
225                 230                 235                 240

Lys Gln His Ala Asp Val Val Ile Glu Val Leu Pro Thr Glu Leu Ile
                245                 250                 255

Pro Asp Asp Asp Glu Gly Lys Val Leu Arg Val Arg Met Ile Gln Lys
            260                 265                 270

Glu Gly Val Lys Phe Phe Asn Pro Val Tyr Leu Phe Asp Glu Gly Ser
    275                 280                 285

Thr Ile Ser Trp Ile Pro Cys Gly Arg Lys Leu Thr Cys Ser Tyr Pro
290                 295                 300

Gly Ile Lys Phe Ser Tyr Gly Pro Asp Thr Phe Tyr Gly Asn Glu Val
305                 310                 315                 320

Thr Val Val Glu Met Asp Gly Met Phe Asp Arg Leu Asp Glu Leu Ile
                325                 330                 335

Tyr Val Glu Ser His Leu Ser Asn Leu Ser Thr Lys Phe Tyr Gly Glu
            340                 345                 350

Val Thr Gln Gln Met Leu Lys His Gln Asn Phe Pro Gly Ser Asn Asn
    355                 360                 365

Gly Thr Gly Phe Phe Gln Thr Ile Ile Gly Leu Lys Ile Arg Asp Leu
            370                 375                 380

Phe Glu Gln Leu Val Ala Ser Arg Ser Thr Ala Thr Ala Thr Ala Ala
385                 390                 395                 400

Lys Ala

<210> SEQ ID NO 5
<211> LENGTH: 396
<212> TYPE: PRT
<213> ORGANISM: Phaeodactylum tricornutum

<400> SEQUENCE: 5

Met Lys Phe Ala Val Phe Ala Ser Leu Thr Ala Thr Ala Ala Ala Phe
1               5                   10                  15

Ala Pro Thr Ala Phe Val Pro Ser Asn Leu Arg Gly Val Ala Pro Ser
            20                  25                  30

Ala Ser Ser Leu Asn Met Ala Leu Lys Glu Gly Gln Thr Pro Ile Ile
        35                  40                  45

Ile Gly Val Ala Ala Asp Ser Gly Cys Gly Lys Ser Thr Phe Met Arg
50                  55                  60

Arg Leu Thr Asn Ile Phe Gly Gly Asp Val Val Gly Pro Leu Gly Gly
65                  70                  75                  80

Gly Phe Asp Lys Gly Ser Trp Glu Thr Asn Thr Leu Val Ser Asp Leu
            85                  90                  95

Thr Thr Val Ile Cys Leu Asp Asp Tyr His Leu Asn Asp Arg Ala Gly
            100                 105                 110

Arg Lys Val Thr Met Arg Thr Ala Leu Asp Pro Glu Glu Asn Asn Phe
        115                 120                 125

Asp Leu Met Tyr Glu Gln Val Lys Ala Leu Lys Asp Gly Lys Thr Val
130                 135                 140

Glu Lys Pro Ile Tyr Asn His Val Asn Gly Thr Leu Asp Thr Pro Glu
145                 150                 155                 160

Thr Ile Glu Pro Thr Pro Ile Ile Phe Glu Gly Leu His Pro Met
            165                 170                 175

His Asp Lys Arg Val Leu Asp Leu Leu Asp Phe Ser Leu Tyr Leu Asp
            180                 185                 190

Ile Ser Asp Asp Val Lys Leu Asn Trp Lys Val Gln Arg Asp Met Glu
        195                 200                 205

Glu Arg Gly His Ser Met Glu Ser Ile Leu Ala Ser Ile Glu Ala Arg
210                 215                 220

Lys Pro Asp Phe Asp Ala Tyr Ile Asp Pro Gln Lys Gln Leu Ala Asp
225                 230                 235                 240

Leu Ile Ile Glu Val Leu Pro Thr Arg Leu Asp Gln Asp Asp Lys Lys
            245                 250                 255

Thr Leu Arg Val Arg Cys Ile Gln Lys Glu Gly Val Glu Asn Phe Asp
            260                 265                 270

Pro Cys Phe Leu Phe Asp Glu Gly Ser Ser Ile Glu Trp Thr Pro Ala
        275                 280                 285

Pro Thr Lys Leu Ser Ser Pro Ala Pro Gly Ile Lys Leu Ala Tyr Tyr
        290                 295                 300

Pro Glu Glu Phe Phe Gly Lys Asp Ala Gln Val Leu Glu Met Asp Gly
305                 310                 315                 320

Asn Phe Asp Asn Ile Gln Glu Leu Val Tyr Val Glu Ser Ala Leu Ser
            325                 330                 335

```
Asn Thr Lys Thr Lys Phe Tyr Gly Glu Met Thr Gln Ala Met Leu Ala
        340                 345                 350

Leu Ala Thr Ala Pro Gly Ser Asn Asn Gly Thr Gly Leu Met Gln Thr
        355                 360                 365

Leu Ala Ala Phe Ala Ile Arg Asp Ile Tyr Glu Lys Lys Thr Ala Ala
        370                 375                 380

Ala Lys Ala Lys Ala Gly Val Ser Ala Ala Ala
385                 390                 395

<210> SEQ ID NO 6
<211> LENGTH: 375
<212> TYPE: PRT
<213> ORGANISM: Chlamydomonas reinhardtii

<400> SEQUENCE: 6

Met Ala Phe Thr Met Arg Ala Pro Ala Pro Arg Ala Thr Ala Gln Ser
1               5                   10                  15

Arg Val Thr Ala Asn Arg Ala Arg Arg Ser Leu Val Val Arg Ala Asp
            20                  25                  30

Lys Asp Lys Thr Val Val Ile Gly Leu Ala Ala Asp Ser Gly Cys Gly
        35                  40                  45

Lys Ser Thr Phe Met Arg Arg Met Thr Ser Ile Phe Gly Gly Val Pro
    50                  55                  60

Lys Pro Pro Ala Gly Gly Asn Pro Asp Ser Asn Thr Leu Ile Ser Asp
65                  70                  75                  80

Met Thr Thr Val Ile Cys Leu Asp Asp Tyr His Cys Leu Asp Arg Asn
                85                  90                  95

Gly Arg Lys Val Lys Gly Val Thr Ala Leu Ala Pro Glu Ala Gln Asn
            100                 105                 110

Phe Asp Leu Met Tyr Asn Gln Val Lys Ala Leu Lys Glu Gly Lys Ser
        115                 120                 125

Val Asp Lys Pro Ile Tyr Asn His Val Ser Gly Leu Ile Asp Ala Pro
    130                 135                 140

Glu Lys Ile Glu Ser Pro Pro Ile Leu Val Ile Glu Gly Leu His Pro
145                 150                 155                 160

Phe Tyr Asp Lys Arg Val Ala Glu Leu Leu Asp Phe Lys Ile Tyr Leu
                165                 170                 175

Asp Ile Ser Asp Asp Ile Lys Phe Ala Trp Lys Ile Gln Arg Asp Met
            180                 185                 190

Ala Glu Arg Gly His Ser Leu Glu Ser Ile Lys Ser Ile Ala Ala
        195                 200                 205

Arg Lys Pro Asp Phe Asp Ala Tyr Ile Asp Pro Gln Lys Lys Asp Ala
    210                 215                 220

Asp Met Ile Ile Gln Val Leu Pro Thr Gln Leu Val Pro Asp Asp Lys
225                 230                 235                 240

Gly Gln Tyr Leu Arg Val Arg Leu Ile Met Lys Glu Gly Ser Lys Met
                245                 250                 255

Phe Asp Pro Val Tyr Leu Phe Asp Glu Gly Ser Thr Ile Ser Trp Ile
            260                 265                 270

Pro Cys Gly Arg Lys Leu Thr Cys Ser Phe Pro Gly Ile Lys Met Phe
        275                 280                 285

Tyr Gly Pro Asp Thr Trp Tyr Gly Gln Glu Val Ser Val Leu Glu Met
    290                 295                 300

Asp Gly Gln Phe Asp Lys Leu Glu Glu Leu Ile Tyr Val Glu Ser His
```

```
305                 310                 315                 320
Leu Ser Asn Thr Ser Ala Lys Phe Tyr Gly Glu Ile Thr Gln Gln Met
                325                 330                 335

Leu Lys Asn Ser Gly Phe Pro Gly Ser Asn Asn Gly Thr Gly Leu Phe
                340                 345                 350

Gln Thr Ile Val Gly Leu Lys Val Arg Glu Val Tyr Glu Arg Ile Val
                355                 360                 365

Lys Lys Asp Val Val Pro Val
                370                 375

<210> SEQ ID NO 7
<211> LENGTH: 403
<212> TYPE: PRT
<213> ORGANISM: Oryza sativa

<400> SEQUENCE: 7

Met Ala Ile Ser Ser Leu His Ala Thr Thr Ser Leu His Ser Pro Cys
1               5                   10                  15

Thr Thr Asn Thr Ser Phe Arg Gln Asn Gln Val Ile Phe Phe Thr Thr
                20                  25                  30

Arg Ser Asn Arg Arg Gly Ser Thr Arg Tyr Gly Gly Ala Arg Thr Phe
            35                  40                  45

Gln Val Ser Cys Ser Val Asp Lys Pro Val Val Ile Gly Leu Ala Ala
        50                  55                  60

Asp Ser Gly Cys Gly Lys Ser Thr Phe Met Arg Arg Leu Thr Ser Val
65                  70                  75                  80

Phe Gly Gly Ala Ala Glu Pro Pro Lys Gly Gly Asn Pro Asp Ser Asn
                85                  90                  95

Thr Leu Ile Ser Asp Thr Thr Thr Val Ile Cys Leu Asp Asp Tyr His
                100                 105                 110

Ser Leu Asp Arg Thr Gly Arg Lys Glu Lys Gly Val Thr Ala Leu Asp
                115                 120                 125

Pro Arg Ala Asn Asp Phe Asp Leu Met Tyr Glu Gln Val Lys Ala Ile
            130                 135                 140

Lys Glu Gly Lys Ala Ile Glu Lys Pro Ile Tyr Asn His Val Thr Gly
145                 150                 155                 160

Leu Leu Asp Pro Pro Glu Leu Ile Gln Pro Pro Lys Ile Phe Val Ile
                165                 170                 175

Glu Gly Leu His Pro Met Phe Asp Glu Arg Val Arg Asp Leu Leu Asp
                180                 185                 190

Phe Ser Ile Tyr Leu Asp Ile Ser Asp Glu Val Lys Phe Ala Trp Lys
            195                 200                 205

Ile Gln Arg Asp Met Ala Glu Arg Gly His Ser Leu Glu Ser Ile Lys
        210                 215                 220

Ala Ser Ile Glu Ala Arg Lys Pro Asp Phe Asp Ala Phe Ile Asp Pro
225                 230                 235                 240

Gln Lys Gln Tyr Ala Asp Ala Val Ile Glu Val Leu Pro Thr Gln Leu
                245                 250                 255

Ile Pro Asp Asp Asn Glu Gly Lys Val Leu Arg Val Lys Leu Ile Met
                260                 265                 270

Lys Glu Gly Val Lys Asn Phe Asn Pro Val Tyr Leu Phe Asp Glu Gly
            275                 280                 285

Ser Ser Ile Thr Trp Val Pro Cys Gly Arg Lys Leu Thr Cys Ser Tyr
        290                 295                 300
```

```
Pro Gly Ile Lys Phe Ala Tyr Gly Pro Asp Thr Tyr Phe Gly His Glu
305                 310                 315                 320

Val Ser Val Leu Glu Met Asp Gly Gln Phe Asp Arg Leu Asp Glu Leu
                325                 330                 335

Ile Tyr Val Glu Ser His Leu Ser Asn Leu Ser Thr Lys Phe Tyr Gly
                340                 345                 350

Glu Val Thr Gln Gln Met Leu Lys His Ala Asp Phe Pro Gly Ser Asn
                355                 360                 365

Asn Gly Thr Gly Leu Phe Gln Thr Ile Val Gly Leu Lys Ile Arg Asp
                370                 375                 380

Leu Tyr Glu Gln Ile Ile Ala Glu Arg Ala Gly Ala Pro Thr Glu Ala
385                 390                 395                 400

Ala Lys Val

<210> SEQ ID NO 8
<211> LENGTH: 52
<212> TYPE: PRT
<213> ORGANISM: Artificial Sequence
<220> FEATURE:
<223> OTHER INFORMATION: bipartite targeting sequence of the
      phoshoribulokinase of Nannochloropsis gaditana (NgPRK BTS)

<400> SEQUENCE: 8

Met Val Lys Thr Ala Ala Val Ser Leu Leu Ala Leu Ala Gly Leu Ala
1               5                   10                  15

Ser Ala Phe Val Pro Pro Thr Thr Asn Phe Arg Ser Ala Asn Arg Trp
                20                  25                  30

Thr Ile Lys Ala Lys Asp Thr Ser Phe Thr Arg Asn Leu Met Met Lys
                35                  40                  45

Leu Gly Ala Asp
    50

<210> SEQ ID NO 9
<211> LENGTH: 156
<212> TYPE: DNA
<213> ORGANISM: Nannochloropsis gaditana

<400> SEQUENCE: 9
atggtcaaga ctgccgccgt aagcctcctg gccctagccg gctcgcatc tgccttcgtg      60 ccccccacca cgaattttcg cagcgctaac agatggacga ttaaggccaa agacacgtcc    120
ttcacccgca acctcatgat gaagctgggc gcggac                              156

<210> SEQ ID NO 10
<211> LENGTH: 720
<212> TYPE: DNA
<213> ORGANISM: Artificial Sequence
<220> FEATURE:
<223> OTHER INFORMATION: codon-optimized (for expression in
      Nannochloropsis) eYFP

<400> SEQUENCE: 10
atggtctcca agggcgagga gctcttcacc ggcgtcgtcc ccatcctcgt cgagctcgac      60
ggcgacgtca acggccacaa gttctccgtc tccggcgagg gcgagggcga cgctacctac    120
ggcaagctca ccctcaagtt catctgcacc accggcaagc tccccgtccc ctggcccacc    180
ctcgtcacca ccttcggcta cggcctccag tgcttcgctc gctaccccga ccacatgaag    240
cagcacgact tcttcaagtc cgctatgccc gagggctacg tccaggagcg caccatcttc    300
ttcaaggacg acggcaacta caagacccgc gctgaggtca agttcgaggg cgacaccctc    360
```

| gtcaaccgca tcgagctcaa gggcatcgac ttcaaggagg acggcaacat cctcggccac | 420 |
| aagctcgagt acaactacaa ctcccacaac gtctacatca tggctgacaa gcagaagaac | 480 |
| ggcatcaagg tcaacttcaa gatccgccac aacatcgagg acggctccgt ccagctcgct | 540 |
| gaccactacc agcagaacac ccccatcggc gacggccccg tcctcctccc cgacaaccac | 600 |
| tacctctcct accagtccgc tctctccaag gaccccaacg agaagcgcga ccacatggtc | 660 |
| ctcctcgagt tcgtcaccgc tgctggcatc accctcggca tggacgagct ctacaagtaa | 720 |

<210> SEQ ID NO 11
<211> LENGTH: 31
<212> TYPE: DNA
<213> ORGANISM: Artificial Sequence
<220> FEATURE:
<223> OTHER INFORMATION: Primer eYFP Fw2

<400> SEQUENCE: 11

| ccgccggaat tcatggtctc caagggcgag g | 31 |

<210> SEQ ID NO 12
<211> LENGTH: 35
<212> TYPE: DNA
<213> ORGANISM: Artificial Sequence
<220> FEATURE:
<223> OTHER INFORMATION: Primer eYFP Rev2

<400> SEQUENCE: 12

| gaaagtccat atgttacttg tagagctcgt ccatg | 35 |

<210> SEQ ID NO 13
<211> LENGTH: 5198
<212> TYPE: DNA
<213> ORGANISM: Artificial Sequence
<220> FEATURE:
<223> OTHER INFORMATION: pCT2Ng vector

<400> SEQUENCE: 13

| gtggcacttt tcggggaaat gtgcgcggaa cccctatttg tttatttttc taaatacatt | 60 |
| caaatatgta tccgctcatg agacaataac cctgataaat gcttcaataa tattgaaaaa | 120 |
| ggaagagtat gagtattcaa catttccgtg tcgcccttat tcccttttttt gcggcatttt | 180 |
| gccttcctgt ttttgctcac ccagaaacgc tggtgaaagt aaaagatgct gaagatcagt | 240 |
| tgggtgcacg agtgggttac atcgaactgg atctcaacag cggtaagatc cttgagagtt | 300 |
| ttcgccccga agaacgtttt ccaatgatga gcacttttaa agttctgcta tgtggcgcgg | 360 |
| tattatcccg tattgacgcc gggcaagagc aactcggtcg ccgcatacac tattctcaga | 420 |
| atgacttggt tgagtactca ccagtcacag aaaagcatct tacggatggc atgacagtaa | 480 |
| gagaattatg cagtgctgcc ataaccatga gtgataacac tgcggccaac ttacttctga | 540 |
| caacgatcgg aggaccgaag gagctaaccg cttttttgca acatggggg atcatgtaa | 600 |
| ctcgccttga tcgttgggaa ccggagctga atgaagccat accaaacgac gagcgtgaca | 660 |
| ccacgatgcc tgtagcaatg gcaacaacgt tgcgcaaact attaactggc gaactactta | 720 |
| ctctagcttc ccggcaacaa ttaatagact ggatggaggc ggataaagtt gcaggaccac | 780 |
| ttctgcgctc ggcccttccg gctggctggt ttattgctga taaatctgga gccggtgagc | 840 |
| gtgggtctcg cggtatcatt gcagcactgg ggccagatgg taagccctcc cgtatcgtag | 900 |
| ttatctacac gacggggagt caggcaacta tggatgaacg aaatagacag atcgctgaga | 960 |

```
taggtgcctc actgattaag cattggtaac tgtcagacca agtttactca tatatacttt    1020
agattgattt aaaacttcat ttttaattta aaaggatcta ggtgaagatc cttttttgata   1080 atctcatgac caaaatccct taacgtgagt tttcgttcca ctgagcgtca gacccccgtag   1140 aaaagatcaa aggatcttct tgagatcctt ttttctgcg cgtaatctgc tgcttgcaaa    1200
caaaaaaacc accgctacca gcggtggttt gtttgccgga tcaagagcta ccaactcttt   1260
ttccgaaggt aactggcttc agcagagcgc agataccaaa tactgtcctt ctagtgtagc   1320
cgtagttagg ccaccacttc aagaactctg tagcaccgcc tacatacctc gctctgctaa   1380
tcctgttacc agtggctgct gccagtggcg ataagtcgtg tcttaccggg ttggactcaa   1440
gacgatagtt accggataag gcgcagcggt cgggctgaac ggggggttcg tgcacacagc   1500
ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagagcg cacgagggag cttccagggg gaaacgcctg gtatctttat agtcctgtcg   1680
ggtttcgcca cctctgactt gagcgtcgat ttttgtgatg ctcgtcaggg gggcggagcc   1740
tatgaaaaaa cgccagcaac gcggccttttt tacggttcct ggccttttgc tggccttttg   1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgagcgcaac gcaattaatg   2040
tgagttagct cactcattag gcaccccagg ctttacactt tatgcttccg gctcgtatgt   2100
tgtgtggaat tgtgagcgga taacaatttc acacaggaaa cagctatgac catgattacg   2160
ccaagcgcgc aattaaccct cactaaaggg aacaaaagct ggagctcagc tgctgccccg   2220
accgtatctc caagtcagac atgaaatctt cagttgcgtt aaaaactcta cgatgctacc   2280
agcgttaaat aaccttgccc acgcctttaa acgtacccga tcattaacat atcgactggc   2340
tgccttggct ttgcaccagc catcatcaga cttaacgatg ggtatgttgc ttgccttttcc   2400 tgcttgaagg gggtccgact ctctgctttc tcgatcgcgg gtgtgacctc tgaattggaa   2460
tgtaaaaatg taagaagcga cgtgtccggt aaagaaatgc ccaagctcca tcaaatctgc   2520
gttgtcggcg accaaaccat gctggctcgt cgacctgccc cggatgcagg agcatggcac   2580
tcggcggcat ggcacttgag cctcgcggga ggaatgtgtg tggttgggcg caggctgtgg   2640
acggcccccc tccagcgaag cggtcgcctc ccttccgac gctttgtgca cgttgtctgg   2700
tgtcctctgt ctcacgcacc tcttcaccga cgtggtgtcc ctcttgttgc tggtgaggga   2760
cttggaatgt ggtcctggtt ctatcctggg cgcgtgtgtt cctttttttc tctaccgtta   2820
ttctctccat ttctgatgtc tcaccaccat ctccctcacc ctccaaccgc gtcgttgtgc   2880
caaaatcata cagcaggatc gatggccaag ttgaccagtg ccgttccggt gctcaccgcg   2940
cgcgacgtcg ccggagcggt cgagttctgg accaccggc tcgggttctc ccgggacttc    3000
gtggaggacg acttcgccgg tgtggtccgg gacgacgtga ccctgttcat cagcgcggtc   3060
caggaccagg tggtgccgga caacaccctg gcctgggtgt gggtgcgcgg cctgacgag    3120 ctgtacgccg agtggtcgga ggtcgtgtcc acgaacttcc gggacgcctc cgggccggcc   3180
atgaccgaga tcggcgagca gccgtggggg cgggagttcg ccctgcgcga cccgccggcc   3240
aactgcgtgc acttcgtggc cgaggagcag gactaaatcg atcttcctta aaaatttaat   3300
tttcattagt tgcagtcact ccgctttggt ttcacagtca ggaataacac tagctcgtct   3360
```

```
tcaccatgga tgccaatctc gcctattcat ggtgtataaa agttcaacat ccaaagctag    3420
aacttttgga aagagaaaga atatccgaat agggcacggc gtgccgtatt gttggagtgg    3480
actagcagaa agtgaggaag gcacaggatg agttttctcg agagctgctg ccccgaccgt    3540
atctccaagt cagacatgaa atcttcagtt gcgttaaaaa ctctacgatg ctaccagcgt    3600
taaataacct tgcccacgcc tttaaacgta cccgatcatt aacatatcga ctggctgcct    3660
tggctttgca ccagccatca tcagacttaa cgatgggtat gttgcttgcc tttcctgctt    3720
gaagggggtc cgactctctg ctttctcgat cgcgggtgtg acctctgaat tggaatgtaa    3780
aaatgtaaga agcgacgtgt ccggtaaaga aatgcccaag ctccatcaaa tctgcgttgt    3840
cggcgaccaa accatgctgg ctcgtcgacc tgccccggat gcaggagcat ggcactcggc    3900
ggcatggcac ttgagcctcg cgggaggaat gtgtgtggtt gggcgcaggc tgtggacggc    3960
ccccctccag cgaagcggtc gcctcccttt ccgacgcttt gtgcacgttg tctggtgtcc    4020
tctgtctcac gcacctcttc accgacgtgg tgtccctctt gttgctggtg agggacttgg    4080
aatgtggtcc tggttctatc ctgggcgcgt gtgttccttt ttttctctac cgttattctc    4140
tccatttctg atgtctcacc accatctccc tcaccctcca accgcgtcgt tgtgccaaaa    4200
tcatacagca ggaggcctgt cgacggcgcg ccggatccag atctgaattc gatatcacgc    4260
gtccatggca tatggctagc gcggccgcct cgagtctaga cttccttaaa aatttaattt    4320
tcattagttg cagtcactcc gctttggttt cacagtcagg aataacacta gctcgtcttc    4380
accatggatg ccaatctcgc ctattcatgg tgtataaaag ttcaacatcc aaagctagaa    4440
cttttggaaa gagaaagaat atccgaatag ggcacggcgt gccgtattgt tggagtggac    4500
tagcagaaag tgaggaaggc acaggatgag ttttctcgag gtacccaat cgccctata     4560 gtgagtcgta ttacgcgcgc tcactggccg tcgttttaca acgtcgtgac tgggaaaacc    4620
ctggcgttac ccaacttaat cgccttgcag cacatccccc tttcgccagc tggcgtaata    4680
gcgaagaggc ccgcaccgat cgcccttccc aacagttgcg cagcctgaat ggcgaatggg    4740
acgcgccctg tagcggcgca ttaagcgcgg cgggtgtggt ggttacgcgc agcgtgaccg    4800
ctacacttgc cagcgcccta gcgcccgctc ctttcgcttt cttcccttcc tttctcgcca    4860
cgttcgccgg ctttccccgt caagctctaa atcgggggct ccctttaggg ttccgattta    4920
gtgctttacg gcacctcgac cccaaaaaac ttgattaggg tgatggttca cgtagtgggc    4980
catcgccctg atagacggtt tttcgccctt tgacgttgga gtccacgttc tttaatagtg    5040
gactcttgtt ccaaactgga acaacactca accctatctc ggtctattct tttgatttat    5100
aagggatttt gccgatttcg gcctattggt taaaaatga gctgatttaa caaaaattta    5160
acgcgaattt taacaaaata ttaacgctta caattag                              5198

<210> SEQ ID NO 14
<211> LENGTH: 891
<212> TYPE: DNA
<213> ORGANISM: Artificial Sequence
<220> FEATURE:
<223> OTHER INFORMATION: pCT55 cassette

<400> SEQUENCE: 14
gaattcatga gatccttttg catcgcagcc ttttggctg tggcatctgc cttcaccaca      60
cagccaactt ccttcactgt gaagactgcg aatgtgggcg aacgggcgag tggggttttc    120
cctgagcaga gctctgctca tcgcacgcgt aaagcaacga ttgtcatggt ctccaagggc    180
```

```
gaggagctct tcaccggcgt cgtccccatc ctcgtcgagc tcgacggcga cgtcaacggc      240
cacaagttct ccgtctccgg cgagggcgag ggcgacgcta cctacggcaa gctcacccrc      300
aagttcatct gcaccaccgg caagctcccc gtccctggc ccaccctcgt caccaccttc       360
ggctacggcc tccagtgctt cgctcgctac cccgaccaca tgaagcagca cgacttcttc      420
aagtccgcta tgcccgaggg ctacgtccag gagcgcacca tcttcttcaa ggacgacggc      480
aactacaaga cccgcgctga ggtcaagttc gagggcgaca ccctcgtcaa ccgcatcgag      540
ctcaagggca tcgacttcaa ggaggacggc aacatcctcg gccacaagct cgagtacaac      600
tacaactccc acaacgtcta catcatggct gacaagcaga gaacggcat caaggtcaac       660 ttcaagatcc gccacaacat cgaggacggc tccgtccagc tcgctgacca ctaccagcag      720 aacacccca tcggcgacgg ccccgtcctc ctccccgaca ccactacct ctcctaccag        780 tccgctctct ccaaggaccc caacgagaag cgcgaccaca tggtcctcct cgagttcgtc      840
accgctgctg catcacccct cggcatggac gagctctaca gtaacatat g                891
```

```
<210> SEQ ID NO 15
<211> LENGTH: 885
<212> TYPE: DNA
<213> ORGANISM: Artificial Sequence
<220> FEATURE:
<223> OTHER INFORMATION: pCT56 cassette

<400> SEQUENCE: 15
gaattcatgg tcaagactgc cgccgtaagc ctcctggccc tagccgggct cgcatctgcc      60
ttcgtgcccc ccaccacgaa ttttcgcagc gctaacagat ggacgattaa ggccaaagac     120
acgtccttca cccgcaacct catgatgaag ctgggcgcgg acgtctccaa gggcgaggag     180
ctcttcaccg gcgtcgtccc catcctcgtc gagctcgacg gcgacgtcaa cggccacaag    240
ttctccgtct ccggcgaggg cgagggcgac gctacctacg gcaagctcac cctcaagttc     300
atctgcacca ccggcaagct ccccgtcccc tggcccaccc tcgtcaccac cttcggctac    360
ggcctccagt gcttcgctcg ctaccccgac acatgaagc agcacgactt cttcaagtcc     420
gctatgcccg agggctacgt ccaggagcgc accatcttct tcaaggacga cggcaactac    480
aagacccgcg ctgaggtcaa gttcgagggc gacaccctcg tcaaccgcat cgagctcaag    540
ggcatcgact tcaaggagga cggcaacatc ctcggccaca agctcgagta caactacaac    600
tcccacaacg tctacatcat ggctgacaag cagaagaacg gcatcaaggt caacttcaag    660
atccgccaca acatcgagga cggctccgtc cagctcgctg accactacca gcagaacacc    720
cccatcggcg acggccccgt cctcctcccc gacaaccact acctctccta ccagtccgct    780
ctctccaagg accccaacga gaagcgcgac cacatggtcc tcctcgagtt cgtcaccgct    840
gctggcatca ccctcggcat ggacgagctc tacaagtaac atatg                     885
```

```
<210> SEQ ID NO 16
<211> LENGTH: 732
<212> TYPE: DNA
<213> ORGANISM: Artificial Sequence
<220> FEATURE:
<223> OTHER INFORMATION: pCT59 cassette

<400> SEQUENCE: 16
gaattcatgg tctccaaggg cgaggagctc ttcaccggcg tcgtccccat cctcgtcgag      60
ctcgacggcg acgtcaacgg ccacaagttc tccgtctccg gcgagggcga gggcgacgct    120
acctacggca agctcacccr caagttcatc tgcaccaccg gcaagctccc cgtcccctgg    180
```

-continued

```
cccaccctcg tcaccacctt cggctacggc ctccagtgct tcgctcgcta ccccgaccac    240
atgaagcagc acgacttctt caagtccgct atgcccgagg ctacgtcca ggagcgcacc    300 atcttcttca aggacgacgg caactacaag cccgcgctg aggtcaagtt cgagggcgac    360
accctcgtca accgcatcga gctcaagggc atcgacttca aggaggacgg caacatcctc    420
ggccacaagc tcgagtacaa ctacaactcc cacaacgtct acatcatggc tgacaagcag    480
aagaacggca tcaaggtcaa cttcaagatc cgccacaaca tcgaggacgg ctccgtccag    540
ctcgctgacc actaccagca gaacaccccc atcggcgacg gccccgtcct cctccccgac    600
aaccactacc tctcctacca gtccgctctc tccaaggacc caacgagaa gcgcgaccac    660 atggtcctcc tcgagttcgt caccgctgct ggcatcaccc tcggcatgga cgagctctac    720
aagtaacata tg                                                        732
```

<210> SEQ ID NO 17
<211> LENGTH: 20
<212> TYPE: DNA
<213> ORGANISM: Artificial Sequence
<220> FEATURE:
<223> OTHER INFORMATION: Primer Cass02Ng Fw
<400> SEQUENCE: 17

```
cttggaatgt ggtcctggtt                                                 20
```

<210> SEQ ID NO 18
<211> LENGTH: 20
<212> TYPE: DNA
<213> ORGANISM: Artificial Sequence
<220> FEATURE:
<223> OTHER INFORMATION: Primer eYFP Rev
<400> SEQUENCE: 18

```
gaacttgagg gtgagcttgc                                                 20
```

<210> SEQ ID NO 19
<211> LENGTH: 70
<212> TYPE: PRT
<213> ORGANISM: Artificial Sequence
<220> FEATURE:
<223> OTHER INFORMATION: In silico protein sequence of first 70 amino
      acids of Nannochloropsis gaditana phosphoribulokinase <400> SEQUENCE: 19

```
Met Val Lys Thr Ala Ala Val Ser Leu Leu Ala Leu Ala Gly Leu Ala
1               5                   10                  15

Ser Ala Phe Val Pro Pro Thr Thr Asn Phe Arg Ser Ala Asn Arg Trp
            20                  25                  30

Thr Ile Lys Ala Lys Asp Thr Ser Phe Thr Arg Asn Leu Met Met Lys
        35                  40                  45

Leu Gly Ala Asp Asp Lys Val Ile Leu Ile Gly Val Ala Ala Asp Ser
    50                  55                  60

Gly Cys Gly Lys Ser Thr
65                  70
```